United States Patent [19]

Young

[11] Patent Number: 5,698,198

[45] Date of Patent: Dec. 16, 1997

[54] METHOD FOR TREATING GRAM NEGATIVE BACTERIAL INFECTIONS IN HUMANS

[75] Inventor: Lowell S. Young, San Francisco, Calif.

[73] Assignee: The Regents of the University of California, Berkeley, Calif.

[21] Appl. No.: 466,327

[22] Filed: Jun. 6, 1995

Related U.S. Application Data

[63] Continuation of Ser. No. 277,934, Jul. 1, 1994, Pat. No. 5,484,591, which is a continuation of Ser. No. 154,142, Nov. 18, 1993, abandoned, which is a continuation of Ser. No. 798,031, Nov. 19, 1991, abandoned, which is a continuation of Ser. No. 306,712, Feb. 3, 1989, abandoned, which is a continuation of Ser. No. 855,878, Apr. 24, 1986, Pat. No. 4,918,163, which is a continuation-in-part of Ser. No. 781,242, Sep. 27, 1985, Pat. No. 4,777,136.

[51] Int. Cl.$^6$ .......................... A61K 39/40; A61K 48/00; C07K 16/12; C12N 15/12
[52] U.S. Cl. .................................. 424/150.1; 424/164.1; 530/388.4; 435/340
[58] Field of Search ............................... 424/150.1, 164.1, 424/169.1, 170.1; 530/388.4, 809; 435/340

[56] References Cited

U.S. PATENT DOCUMENTS

| | | | |
|---|---|---|---|
| H1198 | 6/1993 | Larrich et al. | 530/388.4 |
| 4,428,931 | 1/1984 | Tolman et al. | |
| 4,443,549 | 4/1984 | Sadowski . | |
| 4,464,465 | 8/1984 | Lostrom . | |
| 4,525,453 | 6/1985 | Guardino et al. | |
| 4,574,116 | 3/1986 | Kaplan et al. | |
| 4,587,121 | 5/1986 | Collins et al. | |
| 4,617,264 | 10/1986 | Whiteley et al. | |
| 4,647,447 | 3/1987 | Gries et al. | |
| 4,652,518 | 3/1987 | Makela et al. | |
| 4,683,196 | 7/1987 | McLaughlin . | |
| 4,689,299 | 8/1987 | Insel et al. | |
| 5,057,598 | 10/1991 | Pollack et al. | |

FOREIGN PATENT DOCUMENTS

| | | |
|---|---|---|
| 0101039 | 2/1984 | European Pat. Off. |
| 0163493 | 12/1985 | European Pat. Off. |
| 0174204 | 3/1986 | European Pat. Off. |
| 0176365 | 4/1986 | European Pat. Off. |
| 0183876 | 6/1986 | European Pat. Off. |
| 84/04458 | 11/1984 | WIPO . |
| 85/01659 | 4/1985 | WIPO . |
| 86/03754 | 7/1986 | WIPO . |

OTHER PUBLICATIONS

Thorpe, R. TiBTECH, vol. 11, Feb. 1993, pp. 40–42.
Sloan, A., The Washington Post, Tuesday Jan. 19, 1993, D3.
Spalding, B. J., Bio/Technology, vol. 11:428–429, Apr. 1993
Science, vol. 259:1243, Feb. 26, 1993.
Wenzel, The New England Journal of Medicine, vol. 326(17):1151–1152, Apr. 23, 1992.
Warren et al., The New England Journal of Medicine, vol. 326(17):1153–1157, Apr. 23, 1992.
Ziegler, E.J., JID, 158 (2):285–290, Aug. 1988.
Baumgartner et al., J. Exp. 889–896, Mar. 1, 1990.
N. H. Teng et al., Proc. Nat'l Acad. Sci. USA, 82:1790–1794 (1985).
E. J. Ziegler et al., New England Journal of Medicine, 307:1225–1230 (1982).
A. I. Braude et al., Proc. of the First Inter'l Symposium on Pathophysiology of Combined Injury and Trauma, pp. 364–379 (1983).
San Francisco Chronicle, "Scientists Create a Killer of Poisons", p. 8, (Mar. 21, 1985).
Stanford University Campus Report, "Protein Attacks Bacterial Poison," (Mar. 20, 1985).
R. L. Kirkman et al., Transplantation, 36:620–626 (1983).
E. D. Ball et al., Blood, 62:1203–10 (1983).
L. S. Young, Clinical Research, 32:518A (1984).
L. S. Young, Infection, 12:303–308 (1984).
Ziegler et al., The New England Journal of Medicine, vol. 326, No. 17, p. 1165 (Apr. 23, 1992).
Campbell, Chapter 4 of "MonoclonalAntibody Technology", vol. 13 of Lab Techniques in Biochemistry and Mol. Biol., (Burden et al., Eds. ), Elsevier Press, Netherlands pp. 86–100. (1984).
Pollack et al., J. Clin. Invest. 72, 1874–81. (1983).
Miner et al., Infect. Immun., (Apr. 1986), 52:56–62).
Dunn et al., Arch. Surg. (Jan. 1986), 121:58–62.
Dunn et al., Surgery. (Aug. 1984), 98:283–90.
Peters et al., Infect. Immun. (Nov. 1985), 50:459–66.
Gigliotti and Shenep., J. Infect. Dis., (Jun. 1985), 151:1005–11.
Teng et al., Proc. Nat. Acad. Sci. U.S.A., (Mar. 1985), 82:1790–94.

(List continued on next page.)

*Primary Examiner*—Susan A. Loring
*Attorney, Agent, or Firm*—Townsend and Townsend and Crew LLP

[57] ABSTRACT

The present invention provides novel hybridoma cell lines which produce monoclonal antibodies (MoAbs) that bind epitopes found on lipopolysaccharide most commonly associated with the endotoxin core of gram negative bacteria and exhibit broad cross-reactivity with gram negative bacteria of different genera and effectively neutralize endotoxin. At least one of the MoAbs disclosed (XMMEN-J5D) binds an epitope also found on gram positive bacteria. The hybridomas are produced by fusing an immortal cell, a cell having the ability to replicate indefinitely in myeloma cell culture, and an effector immune cell following immunization of the immune cell host with a preparation of a gram negative bacteria. While several individual hybridoma cell lines producing monoclonal antibodies to lipopolysaccharide are described, the present invention adds to the state of the art an entire family of hybridomas producing monoclonal antibodies to lipopolysaccharide-associated epitopes. The monoclonal antibodies produced by the hybridoma cell lines of the present invention are useful in the detection of bacterial infections, therapy and prophylaxis of bacterial endotoxemia and infection caused by gram negative bacteria.

2 Claims, No Drawings

OTHER PUBLICATIONS

Sadoff et al., Antibiot. Chemother., (1985), 36:134–146. Abstracts of the 24th Interscience Confernce on Antimicrobial Agents and Chemotherapy. (1984), 106: Black and Cannon, "Monoclonal Antibody to Common Pathogenic Neisserna Antigen (H8Ag) Protects Against Memingococcemia (ME) in Mice".
Kim et al., "Studies of the Protective Mechanism of Monoclonal Antibodies Against E. coli".
Sawada et al., J. Infect. Dis. (1984), 150:570–76.
Pollack et al., J. Clin. Invest. (1983), 72:1874–81.
Young et al., Clin. Res. (1982), 30:518A.
Mackie et al., J. Immunol. (1982), 129:829–32.
Hiernaux et al., Eur. J. Immunology, (1982), 12:797–803.
Hancock et al., Infect. Immun. (1982), 37:166–71.
Apicella et al., Infect. Immun. (1981), 34:751–56.
Abe et al., Jpn. J. Exp. Med., (1975), 45:355–359.
Feingold et al., Arch. Int. Med. (1965), 116:326–28.
Zieger et al., 1973, J. Immunol. 111:433–438.
Young et al., 1974, Experientia, 30:192–193.
Chester and Medadow, 1975, Eru. J. Biochem. 58:273–282.
Young, 1975, Inect. Immun., 12:88–92.
Young et al., 1975, Proc. Soc. Exp. Biol. Med., 149:389–396.
Young et al., 1975, J. Clin. Investig., 56:850–861.
Ziegler et al., 1975, Trans. Assoc. Am. Physicians, 88:101–108.
Koval et al., 1977, J. Gen. Micro., 98:387–398.
McCabe et al., 1977, J. Infect. Dis. 136:(Suppl):161–166.
Young et al., 1977, J. Infect. Dis., 136:S174–S180.
Young et al., 1977, Annals Intern. Med., 86:456–471.
Pollack and Young, 1979, J. Cli. Investig., 63:276–286.
Welch et al., 1979, Scan. J. Infect. Dis., 11:291–301.
Olsson et al., (1980) Proc. Nat'l Acad. Sci. U.S.A., 77:5429–5431.
Pennington et al., 1981, J. Infect. Dis., 144:599–603.
Gustafsson et al., 1982, Infect. Immun., 38:449–454.
Hiernaux et al., 1982, Proc. Nat'l Acad. Sci. U.S.A., 79:161620.
Morse et al., 1982, J. Infect. Dis. 145:206–216.
Ono et al., 1982, Monoclonal Anibodies to Leptospira, 252:414–424.
Young et al., 1982, Clin. Res., 30:522A.
Brade and Galanos, 1983, J. Med. MMicrobiol. 16:203–210.
Brade et al., 1983, Infect. Immun., 42:250–256.
Glassy et al., 1983, Proc. Nat'l Acad. Sci. U.S.A., 80:627–633.
Huber–Luckac et al., 1983, Infect. Immun. 40:608–612.
Rowe and Meadow, 1983, Eur. J. Biochem. 132:329–337.
Seigneurin et al., 1983, 221:173–175.
Sugasawara et al., 1983, Infect.Immun. 42:863–868.
Teng et al., 1983, Proc.Nat'l Acad. Sci. U.S.A., 80:802–803.
Atchinson et al., Aug. 11, 1984, The Lancet:354–355.
Black et al., Abstract of the 1984 ICAAC, 106:A96.
Brown et al., 1984, Proc. Nat'l Acad. Sci. U.S.A., 81:3214–317.
Dunn et al., 1984, Surgery, 96:440–446.
Foung et al., 1984, J. Immunol. Meth., 70:83–90.
Kim et al., Abstracts of the 1984 ICAAC 106:A92.
Kirkland et al., 1984, J. of Immunology, 132:2590–2592.
Macario et al., 1984, Surv. Synth. Path. Res. 3:119–130.
McCutchan et al., Aug. 11, 1983, The Lancet 802–803.
Meadows et al., 1984, J. Gen. Micro. 130:631–644.
Nurminen et al., 1984, Infect. Immun. 44:609–613.
Williams et al., Abstracts of the 1984 ICAAC 106.
Young 1984, Infection, 12(4):3–8.
Young et al., Clin. Res. 32:518A.
Appelmelk et al., 1985, J. of Immunol. Methods 82:199–207.
Baumgartner et al., 1984, Lancet 2 (8446):59–63.
Brade and Rietschel, 1984, Eur. J. Biochem. 153:249–254.
Dunn et al., 1985, Arch. Surg. 120:50–53.
Foung et al., 1985, J. Infect. Dis. 125:280–285.
Gaffin et al., 1985, Vox Sang, 48:276–283.
Gascon et al., Abstracts of the 1985 ICAAC:16A 77.
Poxton et al., 1985, FEMS Microbiology Letters 27:247–251.
Raubitschek et al., 1985, Vox Sang, 48:305–308.
Sawada et al., 1985, J. Infect. Dis. 152:1290–1299, 152:965–970.
Siadak and Lostrom, 1985, J. Gen. Microbiology, 131:7–15.
Sieber et al., 1985, J. Infect. Dis. 152:954–964.
Sidberry et al., 1985, J. Immunol. Meth 76:299–305.
Stoll et al., 1985, Clin. Res. 33 (2):420A Abstract only.
Thornley et al., 1985, J. Gen Microbiology 131:7–15.
Young, 1985, Rev. Infect. Dis. Supp. 3:S380–S388.
Young, L.S., 1985, Infection 13 (Suppl. 2):224–229.
Young, 1985, Rev. Infect. Dis. 7(Supp. 4):S572–578.
Casali et al., 1986, Science, 234:476–479.
Cote et al., 1986, Proc. Nat'l Acad. Sci. USA, 83:2959–2963.
J.W. Goding, 1986, in Monoclonal Antibodies: Principles and Practice, Chapter 3, pp. 59–62.
Hamil and Maki, 1986, R.A. Proctor, ed. pp. 75, 82, 92–93, 96, 112–113.
DeJongh–Leuvenink et al., 1986, Eur. J. Clin. Microbiol., 5:148–151.
Masuho et al., 186 Biochem. Biophys. Res. Comm. 135:495–500.
Miner et al., 1986, Infect. Immun. 52:56–62.
Sun et al., 1986, Hybridoma, 5:S17–S20.
Stoll et al., 1986, Infect. Immun. 53:656–662.
Thompson et al., 1986, Journal Immunolog. Methods 94:7–12.
Vreede et al., 1986, Eur. J. Clin.Microbiol. 5:131–147.
Wasserman et al., 1986, J. Immunol. Metho. 92:75–283.
Pollack and Hunter, 1983, ICAACOct. 24–26, Abstract No. 614.
Dunn et al., 1983, Surg. Forum 34:142–144.
Ziegler et al., 1987, Clin. Res. 35(3):619A.
Dunn et al., 1988, Transplantation 45(2):424–429.
Pollack et al., 1989, J. Infect. Dis. 159(2):168–188.
Cross et al., 1986, 4th Intl. Symp. on Infections in the Immunocompromised Host, 124A.
Rapson et al., 1986, 4th Intl. Symp. on Infections in the Immunocompromised Host. 125A.
Elkins et al., 1985, Infect. Immun. 48(2):597–600.
Bogard et al., 1987, Infect. Immun. 55(4):899–908.
Shenap et al., 1987, Rev. Infect. Dis. 9(Supp. 5):S639–S643.
Chong et al., 1987, J. Infect. Dis. 156(5):713–719.
Appelmelk et al., 1988, J. Med. Mirobiol. 26:107–114.
Ward et al., 1988, Clin. Exp. Immunol. 72:157–163.
Greisman et al., 1988, J. Infect. Immun. 157 (1):54–64.
Lachman et al., May 5, 1984, Lancet 981–983.
Pennington et al., 1987, J. Infect. Dis. 155(5):973–978.
Collins et al., 1983, J. Trauma 23 (6):530–534.
Gaffin et al., 1984, S.A. Medical J 65:158–161.
Zanotti et al., 1985, J. Surg. Res. 38:113–115.
Gaffin et al., 1981, J. Surg. Res. 31:18–21.
Rietschel et al., 1977, Infect. Immun. 15(1):34–49.
Dunn et al., 1982, Surg. 92:212–219.
Killion et al., 1988, FEMS Micro. Immun. 47:41–54.

McCabe, W.R, 1972, *J. Immun.* 108(3):601–610.
Johns et al., 1977, *Infect. Immun.* 17(1):9–15.
Marks et al., 1982, *J. Clin. Invest.* 69:742–749.
Braude, A.I, 1980 *Adv. Intern. Med.* 26:427–444.
Ziegler et al., 1979, *Eur. J. Cancer* 15:71–76.
Davis et al., 1978, *J. Exp. Med.* 147:1007–1017.
Ziegler et al., 1978, *Trans. Assoc. Amer. Physiol.* 91:253–258.
Ziegler et al., 1975, *Trans. Assoc. Amer. Physiol.* 88:101–108.
Ziegler et al., 1973, *J. Clin. Invest.* 53:3236–3238.
Ziegler et al., 1973, *J. Immun.* 111(2):433–438.
Braude et al., 1973., *J. Infect. Dis.* 128 (Supp):5157–5164.
Braude et al., 1972, *J. Immun.* 108(2):505–512.
Hodgin et al., 1976, *Infect.* 4(1):5–10.
Calandra et al., 1988, *J. Infect. Dis.* 158(2):312–319.
Trautman et al., 1985, Infect. 13 (5):140–145.
Warren et al., 1987, Infect. Immun. 55(7):1668–1673.
Rietschel et al., 1973, J. Immun. 111(5):1349–1360.
Coughln et al., 1987, J. Immun. 139(2):557–561.
Greisman et al., 1978, Proc. Soc. Exp. Biol. Med. 18:482–490.
Dunn, 1987, World J. Surg. 11:233–240.
Sakulramrung et al., 1985, *J. Infect. Dis.* 151 ():995–1004.
Gaumgartner et al., Rev. Infect. Dis. 9(1):194–205.
Glauser, M.P., 1983, Schweiz Med. Wschn. 113(Supp. 14):35–39.

Morris et al., 1986, *Am. J. Vet. Res.* 47(3):544–550.
Wolf et al., 1980, *Curr. Chemother. Infect. Dis.* 1439–1441.
Johns et al., 1983, *J. Infect. Dis.* 147(1):57–67.
Ng et al., 1976, *J. Gen. Microbiol.* 94:107–116.
Appelmelk et al., 1986, Antonie anLeeuwenhoek 52:537–542.
Martinez et al., 1985, *Eur. J. Clin. Microbiol.* 4(2):186–189.
Zinner et al., 1983, MedicalMicrobiology Vo.2, Academic Press., pp. 71–85.
Peter et al., 1982, *Infect.* 10(4):228–232.
Helting et al., 1981, Immunotherapy: A Guide to Immunoglobulin Prophylaxis and Therapy, Academic Press, pp. 141–150.
Mullan et al., 1974, *Infect. Immun.* 10(6):1195–1201.
van Dijk et al., 1981, *J.Med. Microbiol.* 14:381–389.
Mutharia et al., "Monoclonal Antibodies Specific for *Escherichia coli* J5 Lipopolysaccharide: Cross–Reaction with Other Gram–Negative Bacterial Species," Infect. *Immun.*, 45:631–36 (Sep. 1984).
Nelles et al., "Mouse Monoclonal Antibodies Reactive with J5 Lipopolysaccharide Exhibit Extensive Serological Cross–Reactivity with a Variety of Gram–Negative Bacteria," *Infect. Immun.*, 46:677–81 (Dec. 1984).
Sudo et al. *Chem. Abst.* vol. 104 (1986) p. 147,025m.
Fukuda et al. *Chem. Abst.* vol. 104 (1986) p. 147,026n.
Mutharia et al. *Chem. Abst.* vol. 100 (1984) p. 33,069n.
Sawada et al. *Chem. Abst.* vol. 101 (1984) p. 228,262b.

METHOD FOR TREATING GRAM NEGATIVE BACTERIAL INFECTIONS IN HUMANS

CROSS-REFERENCE TO RELATED APPLICATIONS

This application is a continuation of U.S. application Ser. No. 08/277,934, filed Jul. 1, 1994, now U.S. Pat. No. 5,484,591 which is a continuation of U.S. application Ser. No. 08/154,142, filed Nov. 18, 1993, now abandoned, which was a continuation of U.S. application Ser. No. 07/798,031, filed Nov. 20, 1991, now abandoned, which was a continuation of U.S. application Ser. No. 07/306,712, filed Feb. 3, 1989, now abandoned, which was a continuation of U.S. Ser. No. 06/855,878, filed Apr. 24, 1986 which issued as U.S. Pat. No. 4,918,163 and which was a continuation-in-part application of Ser. No. 06/781,242, filed Sep. 27, 1985 which issued as U.S. Pat. No. 4,777,136, the disclosures of which are hereby incorporated by reference.

BACKGROUND OF THE INVENTION

1. Field of the Invention

The present invention relates generally to infectious diseases and, more particularly, to the prevention, diagnosis and treatment of infections caused by gram negative bacteria.

Bacterial sepsis and related septic shock are frequently lethal conditions caused by infections which can result from certain types of surgery, abdominal trauma and immune suppression related to cancer, transplantation therapy or other disease states. It is estimated that over 700,000 patients become susceptible to septic shock-causing bacterial infections each year in the United States alone. Of these, 160,000 actually develop septic shock, resulting in 50,000 deaths annually.

Gram negative bacterial infections comprise the most serious infectious disease problem seen in modern hospitals. Two decades ago, most sepsis contracted in hospitals was attributable to more acute gram positive bacterial pathogens such as Staphylococcus and Streptococcus. By contrast, the recent incidence of infection due to gram negative bacteria, such as *Escherichia coli* and *Pseudomonas aeruginosa*, has increased.

Gram negative bacteria now account for some 200,000 cases of hospital-acquired infections yearly in the United States, with an overall mortality rate in the range of 20% to 60%. The majority of these hospital-acquired infections are due to such gram negative bacilli as *E. coli* (most common pathogen isolated from patients with gram negative sepsis), followed in frequency by *Klebsiella pneumoniae* and *P. aeruginosa*.

Gram negative sepsis is a disease syndrome resulting from the systemic invasion of gram negative rods and subsequent endotoxemia. The severity of the disease ranges from a transient, self-limiting episode of bacteremia to a fulminant, life-threatening illness often complicated by organ failure and shock. The disease is often the result of invasion from a localized infection site, or may result from trauma, wounds, ulcerations or gastrointestinal obstructions. The symptoms of gram negative sepsis include fever, chills, pulmonary failure and septic shock (severe hypotension).

Gram negative infections are particularly common among patients receiving anti-cancer chemotherapy and immunosuppressive treatment. Infections in such immunocompromised hosts characteristically exhibit resistance to many antibiotics, or develop resistance over the long course of the infection, making conventional treatment difficult. The ever increasing use of cytotoxic and immunosuppressive therapy and the natural selection for drug resistant bacteria by the extensive use of antibiotics have contributed to gram negative bacteria evolving into pathogens of major clinical significance.

Fortunately, more than a decade ago, investigators in the United States and Germany demonstrated that gram negative endotoxins of many different bacterial genera have a "common core structure." In other words, while many infectious gram negative organisms contain individual capsule and surface polysaccharides, there is a core lipopolysaccharide (LPS) structure that is widely shared among the diverse gram negative bacterial genera and their endotoxins.

This core structure contains material identified as "lipid A" that is felt to be responsible for all of the biologic properties of "endotoxin," including pyrogenicity, activation of the complement and clotting systems, hypotension and death in experimental animals. This core or LPS structure is therefore significant for at least two reasons; its association with endotoxicity and its conservation in gram negative bacterial genera.

Because antibiotic treatment remains largely suboptimal against gram negative sepsis, particularly that associated with *P. aeruginosa* bacterial infection, (antibiotics are only effective in treating the bacteria and not in reducing the effects of microbial endotoxins) attention has increasingly focused on immunologic methods to prevent and control such infections. Immunotherapy involves the administration of immunoglobulins (antibodies or active fragments thereof) to bolster the host's native defenses against the toxic effects of the bacteria, for example, by enhancing opsonization and phagocytosis of the infecting bacterial cells, or by neutralization of the biological effects of LPS. Antibodies, or active fragments thereof, that bind with the core structure or lipid A, i.e., LPS, could have a broad reactivity with a number of gram negative endotoxins.

Antibodies directed against epitopes or antigenic determinants on the O-specific side chains of smooth gram negative bacteria have limited utility for use in immunotherapy. This is because they are effective against only those strains of bacteria having complementary or cross-reactive antigenic determinants. Such strain-specific antibodies are of only limited utility. While the core oligosaccharide and lipid A of all strains are thought to share antigenic determinants, the few previous attempts to produce and utilize monoclonal antibodies reactive with these regions in Pseudomonas have been largely unsuccessful.

Immunoglobulins that bind most of the clinically significant 'gram' negative pathogens are essential to the success of immunotherapy. *P. aeruginosa* organisms, which account for 5% to 15% of bloodstream infections, have at least 16 different serotypes (O-antigenic types). Klebsiella organisms have more than 80 capsular types, and *E. coli* organisms, which are far more common, have more than 130 serotypes.

Patients with bacteremia often do not have a confirmed specific diagnosis as to the type of bacterial infection until bacteriologic results are available, which may take several days. Therapy often must be started based on an empirical diagnosis in order to prevent a patient's condition from rapidly deteriorating during the critical first 24 to 48 hours of illness.

There therefore exists a longstanding need for the production of monoclonal antibodies (MoAb), or active fragments thereof, reactive with an epitope or antigenic determinant present on all important pathogenic strains of gram negative bacteria, thus permitting effective diagnosis, prophylaxis, control of bacterial infection and neutralization of associated endotoxemia attributable to gram negative bacterial genera. It would also be beneficial to have available MoAbs which are cross-reactive with gram positive bacteria useful in the diagnosis, treatment and prevention of bacterial infections generally.

2. Description of the Relevant Literature

Bacterial infections have received widespread treatment in the scientific and patent literature. Much of this treatment has focused on sepsis due to gram negative bacterial endotoxin. The following is a list of relevant articles and published applications and a brief description of each:

EP O 101 039 A2, published Feb. 22, 1984, discloses a monoclonal antibody to *Pseudomonas aeruginosa* and methods for its use in diagnosis and therapy;

WO 84/04458, published Nov. 22, 1984, discloses MoAbs reactive with endotoxin core;

WO 85/01659, published Apr. 25, 1985, discloses MoAbs against endotoxin of gram negative bacteria;

EP O 163 493, published Apr. 12, 1985, discloses human MoAbs against gram negative bacteria and specific for serotypic determinants of lipopolysaccharide useful for treating or preventing *P. aeruginosa* infection;

Feingold, et al., *Arch. Int. Med.* (1965) 116:326–28, describe the use of polyclonal antisera derived from human patients recovering from gram negative infection to effectively treat gram negative sepsis in a human patient;

Abe, et al., *Jpn. J. Exp. Med.* (1975) 45:355–59, describe the use of polyclonal antisera produced in response to immunization of mice with *P. aeruginosa* endotoxin;

Apicella, et al., *Infect. Immun.* (1981) 34:751–56, report the analysis of lipopolysaccharide from *Neisseria gonorrhorae* and *N. meningitidis* using monoclonal antibodies;

Zeigler, et al., *N. Eng. J. Med.* (1982) 307:1225–30, report the results of a double-blind trial wherein gram negative bacteremic human patients were treated with human antiserum prepared by vaccinating healthy donors with heat-killed *E. coli* J5 mutant;

Hancock, et al., *Infect. Immun.* (1982) 37:166–71, describe MoAbs specific for *Pseudomonas aeruginosa* outer membrane antigens;

Hiernaux, et al., *Eur. J. Immunology* (1982) 12:797–803 describe MoAbs specific for *E. coli* 0113 lipopolysaccharide (LPS);

Machie, et al., *J. Immunol.* (1982) 129:829–32, describe MoAbs which bind gram negative bacteria of different genera;

Young, et al., *Clin. Res.* (1982) 30:522A, describe MoAbs prepared using *S. minnesota* RS-95 LPS as the immunogen;

Pollack, et al., *J. Clin. Invest.* (1983) 72:1874–81, report enhanced survival of *P. aeruginosa* septicemia associated with high levels of circulating antibody to *E. coli* endotoxin core;

Sawada, et al., *J. Infect. Dis.* (1984) 150:570–76, report protection in mice against infection with *P. aeruginosa* by passive transfer of MoAbs to lipopolysaccharides and outer membrane proteins;

Three relevant abstracts were included in *Abstracts of the 24th Interscience Conference on Anti-microbial Agents and Chemotherapy* (1984) 106: Black and Cannon, "Monoclonal antibody to common pathogenic neisseria antigen (HSAg) protects against meningococcemia (ME) in mice"; Williams, et al., "Panreactive monoclonal antibody (MCA) to Porin Protein F of *Pseudomonas aeruginosa* (PA): Passive immunotherapy in mice"; and Kim, et al., "Studies of the protective mechanism of monoclonal antibodies against *E. coli*";

Mutharia, et al., *Infect. Immun.* (September 1984) 45:631–36, describe MoAbs cross-reactive with gram negative bacteria of different genera believed to bind lipid A and not reactive with gram positive bacteria;

Nelles and Niswander, *Infect. Immun.* (December 1984) 46:677–81, describe two mouse monoclonal antibodies reactive with lipopolysaccharide derived from the J5 mutant of *E. coli* 0111:B4 which binds lipopolysaccharide from both smooth and rough phenotype, gram negative bacteria;

Young, et al., *Clin. Res.* (1984) 32:518A, describe a MoAb directed against the "core" of glyco-lipid of enterobacterial endotoxin;

Young, L. S., *Clin. Res.* (1984) 32:518A, reports the functional activity of MoAbs against lipopolysaccharide antigens of gram negative bacilli;

Young, L. S., *Principles and Practice of Infectious Disease* (1985) John Wiley and Sons, N.Y., N.Y., pp. 452–75, provides an overview of gram negative sepsis;

Sadoff, et al., *Antibiot. Chemother.* (1985) 36:134–46, describe the characterization of mouse monoclonal antibodies directed against *P. aeruginosa* lipopolysaccharides;

Teng, et al., *Proc. Nat. Aced. Sci. USA* (March 1985) 82:1790–94, report the protection of mice against gram negative bacteremia and endotoxemia with human monoclonal IgM antibodies. The MoAbs showed no significant protection from gram positive bacterial infection;

Giglliotti and Shenep, *J. Infect. Dis.* (June 1985) 151:1005–11, describe MoAbs that bind LPS from *E. coli* rough mutant J5 but do not bind intact smooth strains of *E. coli* 0111:B4 or K1:07;

Peters, et al., *Infect. Immun.* (November 1985) 50:459–66, describe MoAbs to enterobacterial common antigen and *E. coli* lipopolysaccharide outer core and demonstrate a shared antigenic determinant believed to be at least in part 4-linked α-N-acetylglucosamine;

Dunn, et el., *Surgery* (August 1985) 98:283–90, report the production of a strain specific binding MoAb using *E. coli* smooth strain 0111:B4 as the immunogen and the production of a gram negative bacteria cross-reactive MoAb using *E. coli* rough mutant J5 as the immunogen. These MoAbs were not reactive with gram positive bacteria;

Dunn, et el., *Arch. Surg.* (January 1986) 121:58–62, report on the immunotherapy of gram negative sepsis employing a single murine monoclonal IgG antibody, demonstrating reactivity with a variety of gram negative organisms, promotion of phagocytosis and providing protection during experimental gram negative sepsis. Also, the MoAb showed no reactivity with gram positive bacteria tested;

Miner, et al., *Infect. Immune.* (April 1986) 52:56–62, describe the characterization of murine MoAbs to *E. coli* J5.

SUMMARY OF THE INVENTION

The present invention provides novel hybridoma cell lines which produce monoclonal antibodies (MoAbs) that bind epitopes found on lipopolysaccharide most commonly associated with the endotoxin core of gram negative bacteria and exhibit broad cross-reactivity with gram negative bacteria of different genera and effectively neutralize endotoxin. At least one of the MoAbs disclosed (XMMEN-J5D) binds an epitope also found on gram positive bacteria. The hybridomas are produced by fusing an immortal cell, a myeloma cell having the ability to replicate indefinitely in cell culture, and an effector immune cell following immunization of the immune cell host with a preparation of a gram negative bacteria. While several individual hybridoma cell lines producing monoclonal antibodies to lipopolysaccharide are described, the present invention adds to the state of the art an entire family of hybridomas producing monoclonal antibodies to lipopolysaccharide-associated epitopes.

The monoclonal antibodies produced by the hybridoma cell lines of the present invention are useful in the detection of bacterial infections, therapy and prophylaxis of bacterial endotoxemia and infection caused by gram negative bacteria.

DETAILED DESCRIPTION OF THE PREFERRED EMBODIMENTS

The present invention involves certain hybrid cells, and their functional equivalents, capable of producing monoclonal antibodies (MoAbs) which bind one or more epitopes present on lipopolysaccharide (LPS) commonly associated with gram negative bacteria. The invention further provides methods for employing such compounds in the detection, treatment and prevention of bacterial infections.

Hybridoma formation and monoclonal antibody production may be effected by many different techniques which are well-known in the art. Basically, the process involves first obtaining immune cells, such as those from the spleen of a mammal, which have been previously stimulated with an antigen either in vivo or in vitro. These cells are then fused to cells, such as myeloma cells or transformed cells, which are capable of replicating indefinitely in cell culture, thereby producing an immortal, immunoglobulin-secreting cell line. The resulting fused cells, or hybridomas, are cultured and the resulting colonies screened for the production of the desired monoclonal antibodies. Colonies producing such antibodies are cloned, and grown either in vivo or in vitro so as to produce large quantities of antibody (for description of the theoretical basis and practical methodology of fusing such cells, see Köhler and Milstein, *Nature* (1975) 256:495, the disclosures of which are hereby incorporated by reference. While such methods are described in further detail hereinafter, it will be appreciated by those skilled in the art that modifications and additions to the techniques may be made without departing from the scope of the present invention.

Mammalian lymphocytes are immunized by in vivo immunization of the animal or in vitro contact with whole cells or cell extracts of gram negative bacteria or free lipopolysaccharide. Such immunization are repeated as necessary at intervals of up to a few weeks so as to obtain a sufficient titer of antibodies. The cells or cell extracts are carried in appropriate solutions or adjuvants. Following the last antigen boost, the animals are sacrificed and spleen cells removed.

Fusion with mammalian myeloma cells or other fusion partners capable of replicating indefinitely in cell culture is effected by standard and well-known techniques (e.g., Milstein and Köhler, *Eur. J. Immunol.* (1976) 6:511, the disclosures of which are hereby incorporated by reference), for example by using polyethylene glycol (PEG) or other fusing agent. This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described. Enzyme deficiencies may include, for example, thymidine kinase (TK) or hypoxanthine-guanine phosphoribosyl transferase (HGPRT). These deficiencies allow selection for fused cells according to their ability to grow on, for example, hypoxanthine-aminopterin-thymidine medium (HAT). Preferably, the immortal fusion partners utilized are derived from a line which does not secrete immunoglobulin.

Individual fused cells are grown in individual tissue culture wells. Feeder cells, such as irradiated thymocytes or other cells, may be used to increase the viability of the cells. Hybridoma culture supernatents from the individual wells are assayed for antibody binding to purified lipopolysaccharide or whole gram negative bacteria, or by other suitable detection methods known in the art, such as enzyme-linked immunoassay (EIA) and immunodot assay. For the former, culture supernatants are placed in reaction wells which had been coated with lipopolysaccharide. After incubation, the reaction wells are washed, and remaining antibody bound to the antigen is detected through a labelled antibody reactive with the anti-LPS antibody. Appropriate labels include radioisotopes, luminescent substrate such as fluorescing agents and components of enzymatic labels.

The Immunodot method is also utilized to screen for clones expressing anti-LPS antibodies (Towbin, et al., *Immunol. Method* (1984) 72:313, the disclosures of which are hereby incorporated by reference). Purified LPS is applied to cellulose nitrate membrane as "dots" and allowed to dry. After blocking in a gelatin solution, the membranes are sequentially immersed in culture supernatant, an anti-mouse Ig-peroxidase conjugate solution and a 4-chloro-1-naphthal solution, with phosphate-buffered saline (PBS) washes in between. Clones expressing reactive immunoglobulin appear as colored dots. Other screening systems known to those in the art may be utilized.

Large quantities of monoclonal antibodies from secreting hybridomas are produced by injecting the clones into the peritoneal cavity of mice and harvesting the ascites fluid therefrom. The mice, preferably primed with pristane or other tumor-promoter and immunosuppressed chemically or by irradiation, may be of various strains, such as New Zealand Black or Balb/c strains. The ascites fluid is harvested from the mice and the monoclonal antibody purified therefrom, for example, by CM Sepharose column or other chromatographic means. High titers of antibodies may be so recovered. Alternatively, the hybridomas may be cultured in vitro in a variety of ways, utilizing either perfusion cultures or suspension cultures, both in batch or continuous culture processes, and monoclonal antibodies recovered from the culture medium or supernatant.

The monoclonal antibodies so produced have a number of diagnostic and therapeutic uses. They are used as in vitro diagnostic agents to test for the presence of gram negative bacteria or bacteria generally in mammals by subjecting body fluids of tissues or other human-derived substances or fluids to standard immunoassay protocols. Additionally, extracts of inanimate objects of which contamination by bacteria would be detrimental, such as medical devices, foodstuffs or water, may also be tested. Such assays may be of a radioimmunoassay, EIA or chemiluminescent format. In one such assay, body fluid is contacted to antibodies of the present invention and a labelled second antibody used to detect the presence of bacteria to which the antibodies are bound. Alternatively, a competitive immunoassay or a "sandwich" type assay can be employed. Such histochemical methods are well-known in the art; protocols are found, for example, in *Methods in Immunodiagnosis*, 2nd edition, Rose and Bigazzi, eds., John Wiley and Sons, 1980, which is incorporated by reference, and in Campbell et el., *Methods of Immunology*, W. A. Benjamin, Inc., 1964.

Further, monoclonal antibodies of the present invention are used for the in vivo detection of localized areas of bacterial infection, for example, abscesses or cysts in the soft tissue and osteomyelitis in bone. For example, labelled antibody is administered to a mammal suspected of having a bacterial infection. The antibody selectively binds to the bacteria present in the mammal, thereby concentrating the label in the area of infection. Labels appropriate for such use include radioisotopes, such as $^{235}$Iodine, $^{131}$Iodine, $^{99}$Technetium and $^{111}$Indium, which can then be detected using standard radiographic techniques. Alternatively, the monoclonal antibodies can be labelled with paramagnetic contrast agents, and detected by nuclear magnetic resonance methods. The labelled antibodies thus produce a detectable image of the bacterial abscess. Similarly, these monoclonal antibodies may be employed in a method for detecting and quantifying microbial endotoxins in body fluids, secretions, and extracts as well as in drugs, diagnostic agents or liquid intermediates produced in the manufacture of diagnostic and therapeutic agents.

Monoclonal anti-LPS antibodies are used prophylactically in patients at risk for gram negative bacterial infection. Administration of effective amounts of these monoclonal antibodies serves to enhance the body's potential ability to defend against the particular organism, thereby lessening the risk of subsequent infection.

The monoclonal antibodies of the present invention may be used therapeutically to treat potentially lethal bacterial infections and septic shock. The antibodies are administered either intravenously or intramuscularly in a physiologically acceptable solution, either alone or in combination with antibiotics. Although to do so may affect the binding characteristics of the present monoclonal antibodies, they may be lyophilyzed for storage and shipment and reconstituted prior to administration.

Because the monoclonal antibodies have special affinity for lipopolysaccharide, they provide selective treatment for life-threatening symptoms of endotoxemia, such as septic shock associated with gram negative infections, which are otherwise often unresponsive to antibiotic treatment. Among the effects of treatment with several of these monoclonal antibodies are the facilitation of opsonization and phagocytosis of some bacteria, presumably by binding to the bacterial cell wall. The monoclonal antibodies thus aid in combatting the toxic effects of the bacterial infections.

While the foregoing has focused on human applications of the present invention, the inherent utility of the invention in veterinary applications will be obvious to one skilled in the art.

For all such diagnostic, prophylactic and therapeutic uses, the monoclonal antibodies and other necessary reagents and appropriate devices and accessories may be provided in kit form so as to be readily available and easily used.

The following examples are offered by way of illustration and not limitation.

EXPERIMENTAL

EXAMPLE I

HYBRIDOMAS XMMEN-OE5, XMMEN-LY1, AND XMMEN-LY2

A. Production of Hybridomas

Balb/c mice (Charles Rivers, Wilmington, Mass.) were immunized with $1\times10^8$ boiled cells of either *E. coli* J5 - *Salmonella minnesota* R595. The LPS of J5, a mutant of strain *E. coli* O111, and the LPS of R595, an Re mutant of *S. minnesota*, both lack outer O-specific side chains and consist only of the core LPS (lipid A and core oligosaccharide). After primary immunization, the mice were boosted with an intraperitoneal injection of $1\times10^8$ boiled cells lacking O-specific side chains at one month intervals. (The present example focuses on XMMEN-OE5 produced from *E. coli* immunogen rather than XMMEN-LY1 and XMMEN-LY2, both produced from R595 immunogen. Data on prophylaxis against bacterial challenge in MoAbs produced by all three is provided, however.).

Four days following the last antigen boost, spleen cells from an immunized mouse were aseptically removed. Following procedures as outlined elsewhere (St. Groth, *J. Immuno. Meth.* (1980) 35:1, which is incorporated by reference), $5\times10^7$ spleen cells were fused with an equal number of P63Ag8.653, a nonsecreting mouse myeloma cell line of Balb/c origin (American Type Culture Collection, Rockville, Md.), using polyethylene glycol 4000 (Merck and Co., Inc., Rahway, N.J.). Hybrid cells were placed into 96-well culture plates (Costar, Cambridge, Mass. #3596) on medium which had been pre-incubated with a feeder layer of normal Balb/c thymocytes ($1\times10^5$ cells per well, one day before fusion). Cells were cultured at 37° C, in a 10% $CO_2$ atmosphere, in the following medium for the first two weeks. Dulbecco's Modified Eagle's Medium, with glutamine, and glucose at 4.5 g/l (Gibco, Santa Clara, Calif., #320-1965), Fetal Bovine Serum (10%) (Microbiological Associates, Walkerville, Md.), sodium pyruvate (1%) (Gibco, Santa Clara, Calif., #320-1360), penicillin (50μ/ml) —Streptomycin (50μ/ml) (Gibco, Santa Clara, Calif., #600-5070), and hypoxanthine-aminopterin-thymidine (HAT) which was prepared by using hypoxanthine (10 mM) thymidine (1.6 mM) combined with 0.04 mM aminopterin (Sigma Chemical Co., St. Louis, Mo.). Medium for regular maintenance (past two-weeks fusion date) was identical to the above, except that no aminopterin was included in the medium (HT medium).

Between two to four weeks post-fusion, cultures of hybrid cells were tested for antibody binding to purified LPS by EIA and immunodot assay. Cultures that were positive on repeated testing were then cloned by limiting dilution techniques. Briefly, the cells were cultured at varying dilutions between 10–1 cells per well in 96-well tissue culture plates (Costar, Cambridge, Mass., #3596). Wells that contained only one colony were identified by microscopic examination, then tested for anti-J5 or anti-R595 activity by EIA. Positive clones were expanded onto 24-well tissue cultures plates (Costar, Cambridge, Mass. #3524), recloned and retested by the same methods. Three clones, designated XMMEN-OE5, XMMEN-LY1 and XMMEN-LY2 were found to stably secrete monoclonal antibody; the monoclonal antibody was determined to be of immunoglobulin class IgM by radial immunodiffusion and EIA using standard methods. Hybridomas XMMEN-OE5 and XMMEN-LY1 are presently on deposit with the American Type Culture Collection (A.T.C.C.), 12301 Parklawn Dr., Rockville, Md. 20852, USA. The deposit was made on Apr. 24, 1986, and given A.T.C.C. Accession Nos. HB9081 and HB9082, respectively.

Balb/c mice (Charles River) were used to culture the hybridomas intraperitoneally.. Approximately $3\times10^6$ hybridoma cells were injected intraperitoneally (i.p.) into mice that had been pretreated as follows: injected i.p. one week earlier with 0.5 ml of pristane (Aldrich Chemical Co., Milwaukee, Wis.). The resultant ascites fluid, collected 11–15 days after injection of the hybridomas, contained on average 2 mg/ml of the antibody, as determined by radial-immunodiffusion (Meloy, Radial Immunodiffusion, Springfield, Va., Plate #J-304).

The antibody in ascites fluid was purified by fast flow ion exchange chromatography using a CM Sepharose column (Pharmacia, Inc., Piscataway, N.J.) by methods well-known to those skilled in the art.

Utilizing tissue culture medium with high glucose content (DMEM, 0.45% glucose, 2 mM glutamine, 2 mM pyruvate) the cell line was grown in vitro in a 1.5 l conventional chemostat. At a dilution rate of 0.021/hour steady state conditions were maintained where cell concentrations were 5 to 6×10$^5$/ml with 84% viability, MoAb concentration was 25 µg/ml, the volumetric productivity was 0.63 µg MoAb per hour and the specific productivity 30 µg MoAb/10$^6$ cells/day.

B. XMMEN-OE5 MoAb Enzyme Immunoassay (EIA) Inhibition

1. Preparation of antigen-coated EIA plates: *E. coli* J5 lipopolysaccharide (List Biologicals, Campbell, Calif.) was diluted to 20 ug/ml in 0.01 PBS (pH 7.4). 100 ul of this solution was added to each well of EIA reaction plates (Gilford Diagnostics, Oberlin, Ohio), and allowed to incubate overnight at room temperature (RT). On the following day, the plates were washed 2× with PBS, then blocked by adding 150 ul/well of 2% bovine serum albumin (Sigma Chemical Co., St. Louis, Mo.), and allowing this solution to incubate overnight at RT. On the next day, the plates were washed 2× with PBS and either used immediately, or stored at 4° C.

2. Inhibition assay: Purified XMMEN-OE5 monoclonal antibody was diluted to 2 ug/ml in 0.01M PBS, and mixed with graduated amounts of purified antigens (*E. coli* J5 lipopolysaccharide (LPS), *Salmonella minnesota* R 595 LPS, *Salmonella minnesota* R 595 Lipid A, and *Pseudomonas aeruginosa*, Fisher type 1 LPS all from List Biologicals, Campbell, Calif.). These antibody-antigen mixtures were incubated overnight at room temperature.

On the following day, 100 ul of the various antibody-antigen mixtures were added to EIA Wells coated with *E. coli* J5 LPS, and allowed to react for one hour at RT, then washed 2× with PBS. The next step was the addition of 100 ul/well of goat anti-mouse IgM-peroxidase conjugate (Cappel, Malvern, Pa.), which was also allowed to react for one hour at RT. Following a final 3× wash with PBS, enzyme substrate (ABTS, from Boehringer Mannheim, Indianapolis, Ind.) was added @100 ul/well and allowed to react for 45 minutes at RT. Enzyme reaction was stopped by the addition of 100 ul/well of 10 mM sodium azide. Absorbance was recorded at 405 nm, utilizing a Gilford Manual EIA reader. The results are summarized in Table 1.

TABLE 1

Inhibition of XMMEN-OE5 Monoclonal Antibody Binding to Solid-phase J5 LPS, as Determined by Enzyme Immunoassay (EIA) Percent Inhibition

| Inhibitor (ug/ml) | J5 LPS | Re LPS | Lipid A | P. aeruginosa LPS (type 1) |
|---|---|---|---|---|
| 125 | 95 | 98 | 82 | 0 |
| 62 | 92 | 80 | 67 | 0 |
| 31 | 89 | 68 | 58 | 0 |

TABLE 1-continued

Inhibition of XMMEN-OE5 Monoclonal Antibody Binding to Solid-phase J5 LPS, as Determined by Enzyme Immunoassay (EIA) Percent Inhibition

| Inhibitor (ug/ml) | J5 LPS | Re LPS | Lipid A | P. aeruginosa LPS (type 1) |
|---|---|---|---|---|
| 16 | 70 | 60 | 38 | 0 |
| 8 | 54 | 52 | 0 | 0 |
| 4 | 50 | 47 | 0 | 0 |
| 2 | 40 | 44 | 0 | 0 |
| 1 | 40 | 40 | 0 | 0 |
| 0.5 | 22 | 35 | 0 | 0 |
| 0.25 | 0 | 29 | 0 | 0 |

C. XMMEN-OE5 MoAb Immunodot Serology

Antigens were applied to 0.20 um cellulose nitrate membrane (Sartorius) as 1 ul "dots" and allowed to air dry for five minutes. (Concentrations used were: for purified LPS, 100 ug/ml in PBS, for boiled cell preparations, approximately 1×10$^8$ cells/ml.) The antigen spotted membranes were then blocked with a 1% solution (wt/vol PBS) of gelatin (Difco, Detroit, Mich.), for 30 minutes at room temperature (RT). Following a rapid (1 minute each, 2×) wash, XMMEN-OE5 antibody (2–5 ug/ml in PBS) was incubated with the membranes for 30 minutes at RT. The membranes were washed rapidly 3× with PBS, then incubated with goat anti-mouse IgM-peroxidase conjugate (Cappel, Malvern, Pa.) for 30 minutes at RT. After washing the membranes 3–4× with PBS, substrate (4 chloro-1-napthol, Sigma Chemical Co., St. Louis, Mo.) was incubated with the membranes at RT. Positive reactions usually appeared as purple dots within 2–5 minutes, and were visually graded as 4+ (very strong) to 1+ (weak). The results are summarized in Table 2.

TABLE 2

XMMEN-OE5 Monoclonal Antibody Immunodot Serology

| Antigen | Reaction* |
|---|---|
| *Salmonella minnesota* R60 (Ra) LPS | — |
| *Salmonella minnesota* R345 (Rb) LPS | — |
| *Escherichia coli* J5 (Rc) LPS | 2+ |
| *Salmonella minnesota* R7 (Rd) LPS | 1+ |
| *Salmonella minnesota* R595 (Re) LPS | 1+ |
| *Pseudomonas aeruginosa* PAC 605 LPS | 2+ |
| *Pseudomonas aeruginosa* Fisher types 1–7 | — (all types) |
| *Escherichia coli* J5 boiled cells | 3+ |
| *Escherichia coli* 014:K7 boiled cells | 1+ |
| *Pseudomonas aeruginosa* PAC 605 boiled cells | 3+ |
| *Pseudomonas aeruginosa* Fisher 2 boiled cells | — |
| *Acinetobacter calcoaceticus* boiled cells | — |

D. XMMEN-OE5 MoAb Slide Agglutination 100 ul of XMMEN-OE5 monoclonal antibody (0.5 mg/ml in PBS) was mixed with an equal volume of live bacteria cells (approx. 1 × 10$^9$/ml) on a glass slide. Positive agglutination was scored visually within 15 minutes as strong (4+) to weak (1+). The results are summarized in Table 3.

TABLE 3

| XMMEN-OE5 Monoclonal Antibody Slide Agglutination | |
|---|---|
| Antigen | Reaction |
| Escherichia coli J5 | 3+ |
| Escherichia coli 014:K7 | 2+ |
| Escherichia coli 085:H9 | 1+ |
| Pseudomonas aeruginosa PAC 557 | 1+ |
| Pseudomonas aeruginosa Fisher type 2 | 1+ |
| Klebsiella caroli | — |
| Staphylococcus aureus | — |

E. In Vivo Efficacy of XMMEN-OE5 MoAbs

1. Description of the In Vivo Model: For all of the in vivo efficacy studies, female CD-1 mice weighing an average of 20 grams at 4–6 weeks of age were obtained from Charles River Breeding Laboratories. XMMEN-OE5 antibody was injected i.p. in various doses at differing time intervals. The challenge organisms consisted of one of the following:

Pseudomonas aeruginosa strain 3632 which is a Fisher serotype 2, serum resistant organism isolated from a patient at UCLA Medical Center.

Escherichia coli sero-group 014K7 which is a well characterized serum sensitive strain obtained from Dr. Erwin Neter at Buffalo Children's Hospital. This strain is the most common enteric organism isolated from human gram negative infections.

Escherichia coli 04K12 which is a serum resistant, encapsulated organism isolated from a patient at the UCLA Medical Center.

Escherichia coli 085H9 which is a serum resistant organism obtained from the Centers for Disease Control in Atlanta, Ga.

For these studies, the bacteria were neither modified nor incorporated into a mucin challenge. To prepare the bacterial inoculum, organisms were grown for 16–18 hours in trypticase soy agar plates. Bacterial colonies were then harvested by gentle washing using a cotton tipped applicator, centrifuged, resuspended, and finally washed three more times. A stock solution of bacteria was prepared from a suspension that corresponded to an optical density of MacFarland-1. A series of 10-fold dilutions in saline were inoculated onto agar plates to quantitate the organisms in suspension.

Aliquots (0.1 ml) of these dilutions were then inoculated into animals to determine lethality. It was possible to determine an approximate $L_{100}$—the lowest dose of organisms that, in individual challenge experiments, produced a uniformly lethal effect in mice. The $LD_{100}$ dose for each of the gram negative organisms was used in the following studies.

2. Prophylaxis Against Bacterial Challenge: In a series of antibody protection studies, XMMEN-OE5, XMMEN-LY1 and XMMEN-LY2 were administered to mice at intervals ranging from 4 to 18 hours prior to a challenge with an $LD_{100}$ dose of one of four gram negative organisms. The results of these studies, as shown in Tables 4 and 5, demonstrated that these antibodies provided significant protection against three of the four challenging organisms. A summary of each of these studies follows.

1) Treatment: XMMEN-OE5 400 ug (20 mg/kg) i.p. at both 48 hours and 24 hours prior to challenge.

Challenge: Pseudomonas aeruginosa strain 3632 injection i.p. at a dose of $1 \times 10^8$ cells per mouse.

Results: At 48 hours, 4/4 mice that received XMMEN-OE5 survived versus 1/4 mice receiving a saline control.

2) Treatment: XMMEN-OE5 800 ug (40 mg/kg) i.p. at two hours prior to challenge.

Challenge: E. coli strain 014K7 injected i.p. at a dose of $5 \times 10^8$ cells/mouse.

Results: At 48 hours, 7/8 mice that received XMMEN-OE5 survived versus 0/4 animals that received a saline control.

3) Treatment: XMMEN-OE5 400 ug (20 mg/kg) i.p. at both 48 hours and 24 hours prior to challenge.

Challenge: E. coli strain 085:H9 injected i.p. at a dose of $5 \times 10^7$ cells per mouse.

Results: At 48 hours, 5/12 mice that received XMMEN-OE5 survived versus 4/12 mice that received saline control.

4) Treatment: XMMEN-OE5 400 ug (20 mg/kg) i.p. four hours prior to challenge.

Challenge: E. coli strain 04:K12 injected i.p. at a dose of $5 \times 10^7$ cells per mouse.

Results: At 48 hours, 5/5 mice that received XMMEN-OE5 survived versus 1/5 mice that received saline control.

In summary, these studies demonstrated significant protection against three of the four challenge organisms tested—Pseudomonas aeruginosa strain 3632, E. coli strain 014K7 and E. coli strain 04K12—as a result of treatment with XMMEN-OE5 antibody. No significant protection was noted against E. coli strain 085H9 in these experiments.

TABLE 4

| | Survival | |
|---|---|---|
| Challenge | XMMEN-OE5 | CONTROL |
| 1. Pseudomonas | 4/4 | 1/4 |
| 2. E. coli 014K7 | 7/8 | 0/4 |
| 3. E. coli 085H9 | 5/12 | 4/12 |
| 4. E. coli 04K12 | 5/5 | 1/5 |
| | 21/29 | 6/25 |

CD-1 mice (female, approx. 22 g) were injected on day one with 0.4 mg of column purified anti-core endotoxin monoclonal antibody, either XMMEN-LY1 or XMMEN-LY2. Control animals received saline (0.2 ml) on day 2, these same mice were injected with an approximate $LD_{100}$ dose of bacteria (i.p.). Survivors were recorded at 48 hours post-infection.

TABLE 5

Protection with Monoclonal Antibody against Live Bacteria Challenge in CD-1 Mice

| | Survivals | | |
|---|---|---|---|
| Challenge Bacteria | XMMEN-LY1 | XMMEN-LY2 | Control |
| Pseudomonas aeruginosa Fisher Type 2 (#3632) | 4/4 | 3/4 | 1/4 |
| Escherichia coli 014:K7 | 6/8 | 4/8 | 0/4 |
| Escherichia coli 04:K12 | 5/5 | ND | 2/5 |
| Escherichia coli 085:H9 | 2/8 | 1/8 | 2/8 |

3. prophylaxis Against Endotoxin Challenge: The ability of XMMEN-OE5 antibody to neutralize bacterial endotoxin was demonstrated in the same animal model described above. For the neutralization studies, purified endotoxin from the J5 E. coli mutant strain 0111 was obtained from List Laboratories, Campbell, Calif. An $LD_{50}$ value of endotoxin in mice was determined to be 0.25 mg/mouse and the $LD_{100}$ to be 0.50 mg/mouse. Twenty four hours prior to endotoxin challenge, mice received either 800 ug (40 mg/kg) of XMMEN-OE5 or saline control by IP injection. Results, as shown in Table 5, revealed that 12/17 (71%) mice treated with antibody survived the $LD_{50}$ endotoxin challenge versus 7/17 (41%) control mice, whereas 5/17 (29%) mice treated with antibody survived the $LD_{100}$ endotoxin challenge versus 3/17 (18%) control mice. These observations indicate that in a passive protection study, XMMEN-OE5 significantly increased survival after an $LD_{50}$ endotoxin challenge. Furthermore, this protective effect appears to be dependent upon the amount of the endotoxin challenge administered. These results are illustrated below.

TABLE 6

| Challenge | Survival | |
|---|---|---|
| | XMMEN-OE5 | Control |
| 0.25 mg | 12/17 | 7/17 |
| 0.50 mg | 5/17 | 3/17 |
| | 17/34 | 10/34 (P = 0.0384 by one tailed Z test) |

4. Adjuvant Therapy Studies: To assess the therapeutic efficacy of XMMEN-OE5 combined with standard antibiotic therapy administered to mice after the onset of infection, the following series of experiments were performed.

a) Pilot Studies

In a preliminary study, female CD-1 mice were infected with *Pseudomonas aeruginosa* strain 3632 ($1.6 \times 10^8$ cells/mouse). Immediately after challenge, mice received intramuscular antibiotics either alone or in combination with antiendotoxin antibody. The antibiotic regimen consisted of amakacin 1.56. mg/mouse and cefoperazone 12.5 mg/mouse given as single doses. Three hours after challenge, mice received intravenous injections of 0.4 mg of XMMEN-OE5 (20 mg/kg) or saline control. Results of this study demonstrated that 11/15 mice receiving antibiotics plus antiendotoxin antibody survived versus 5/15 mice that received antibiotics alone (P=0.02 by Fisher's exact test).

b) Expanded Therapy Studies

Therapy studies were expanded to incorporate additional gram negative infections. As in the previous study, female CD-1 mice were injected with $LD_{100}$ amounts of live, gram negative bacteria. Two hours after these inoculations, antibiotics or saline controls were injected intramuscularly. Because the four bacterial strains differed in their susceptibility to antibiotics, the following calculated doses of antibiotics were used (in mg/mouse):

| Organism | Antibiotic Dose | |
|---|---|---|
| | Cefoperazone | Amakacin |
| *E. coli* 014K7 | 0.3 | 0.015 |
| *E. coli* 04K12 | 0.8 | 0.2 |
| *E. coli* 085H9 | 0.9 | 0.015 |
| *P. aeruginosa* 3632 | 12.5 | 1.6 |

Four hours after inoculation with a gram negative organisms and two hours after treatment with antibiotics, mice received intravenous injections of either XMMEN-OE5 antibody or saline control. For each of the four gram negative organisms listed above, all five groups of mice received the following series of treatments. Assessments of lethality were made 48 hours after the initial inoculation.

Group 1: $LD_{100}$ of bacteria plus combination antibiotics plus 300 ug of XMMEN-OE5 antibody.

Group 2: $LD_{100}$ of bacteria plus combination of antibiotics plus 75 ug of XMMEN-OE5 antibody.

Group 3: $LD_{100}$ of bacteria plus saline plus 300 ug of XMMEN-OE5 antibody.

Group 4: $LD_{100}$ of bacteria plus combination antibiotics plus saline.

Group 5: $LD_{100}$ of bacteria plus saline plus saline.

c) Results of Expanded Studies

No significant toxicity occurred in any of he more than 250 mice involved in efficacy studies, or in any of the mice, rats, guinea pigs, or nonhuman primates treated in the toxicology studies.

Efficacy experiments used a lot of XMMEN-OE5 antibody with which EIA binding to endotoxin-coated wells was successfully demonstrated. These studies, summarized in Table 7, demonstrated increased survival of mice receiving the higher dose of XMMEN-OE5 plus antibiotics when compared to antibiotics alone.

TABLE 7

| Treatment | Results |
|---|---|
| 1. Antibiotics | 34/56 (61%) |
| XMMEN-OE5 300 ug | Survived 48 Hrs |
| 2. Antibiotics | 28/56 (50%) |
| XMMEN-OE5 75 ug | Survived 48 Hrs |
| 3. XMMEN-OE5 300 ug | 16/56 (29%) |
| Saline Control | Survived 48 Hrs |
| 4. Antibiotics | 25/56 (45%) |
| Saline Control | Survived 48 Hrs |
| 5. Saline Control | 16/56 (29%) |
| Saline Control | Survived 48 Hrs |

Of the four gram negative organisms tested, the least efficacy was observed against *E. coli* 014K7. On the other hand, the 300 ug dose of XMMEN-OE5 plus combination antibiotic therapy was associated with the highest survival rate when the challenge was either of the remaining three organisms—*Pseudomonas aeruginosa* 3632, *E. coli* 08H59, or *E. coli* 04K12 (see Table 8).

5. Summary of Efficacy Experiments: In spite of a significant number of variables inherent in the experimental animal model used in these experiments, XMMEN-OE5 was shown to 1) provide significant protection against several gram negative organisms; 2) neutralize lethal doses of purified endotoxin in a dose dependent manner; and 3) to have moderate efficacy as an adjunct to conventional antibiotics in the treatment of established gram negative infections.

TABLE 8

| TREATMENT | 24 Hours | | | | | | 48 Hours | | | | | |
|---|---|---|---|---|---|---|---|---|---|---|---|---|
| | 3632 | 014K7 | 085H9 | 04K12 | SUR-VIVORS | SUR-VIVORS | 3632 | 014K7 | 085H9 | 04K12 | SUR-VIVORS | SUR-VIVORS |
| Antibiotics XMMEN-OE5 High Dose | 14/14 | 13/14 | 14/14 | 7/14 | 48/56 | 86% | 10/14 | 7/14 | 11/14 | 6/14 | 34/56 | 61% |
| Antibiotics XMMEN-OE5 Low Dose | 13/14 | 10/14 | 13/14 | 10/14 | 36/56 | 64% | 12/14 | 4/14 | 11/14 | 1/14 | 28/56 | 50% |
| Saline XMMEN-OE5 High Dose | 9/14 | 7/14 | 5/14 | 3/14 | 24/56 | 43% | 7/14 | 4/14 | 5/14 | 0/14 | 16/56 | 29% |
| Antibiotics Saline | 13/14 | 14/14 | 11/14 | 5/14 | 43/56 | 77% | 9/14 | 6/14 | 8/14 | 2/14 | 25/56 | 45% |
| Saline Saline | 8/14 | 10/15 | 6/13 | 2/14 | 26/56 | 46% | 5/14 | 6/15 | 4/13 | 1/14 | 16/56 | 29% |

F. Phase I Clinical Trial

Early data from the Phase I clinical trial of monoclonal antibodies produced by hybridoma XMMEN-OE5 are only in anecdotal form but are reported below.

1. The first patient, F. R., was a 60 year old male with suspected gram negative sepsis. He received 0.1 mg/kg (total does 8.5 mg) of XMMEN-OE5 i.v. over one hour. He experienced no adverse effects. Blood cultures subsequently demonstrated that he did not have gram negative bacteremia, but instead had a raging fungemia due to Torulopsis. The fungal abscess was surgically drained and he remained in stable condition three weeks after the administration of antibody.

2. The second patient, T. G., was a 57 year old female with documented gram negative bacteremia and pyelonephritis secondary to ureteral obstruction. She underwent surgical nephrostomy placement and received 0.5 mg/kg (total dose 36 mg) of XMMEN-OE5 i.v. over 1½ hours. She experienced no adverse effects, rapidly defervesced, and remained afebrile 12 hours after infusion. The prompt resolution to her fever is possibly due to the administration of antibody.

3. The third patient, K. S., was a 60 year old female with severe coronary artery disease who was admitted for unstable angina. She underwent coronary artery bypass surgery which was complicated by a transient episode of acute renal failure. Post-operatively she developed a fever of 102.8° and subsequently had Acinetobacter cultured from her blood. Antibiotics were started, and ten days post surgery, she received XMMEN-OE5 0.5 mg/kg (total dose 42 mg) i.v. over 1½ hours. Following antibiotic and anti-endotoxin antibody treatment, blood cultures became negative and her condition steadily improved. She remained in stable condition one week after administration of antibody.

The fourth patient, S. D., was a 60 year old female with persistent gram negative bacteremia (Klebsiella) of unknown etiology, An extensive workup revealed no source of infection, but urinary abnormalities made pyelonephritis the most likely cause. On her third hospital day, despite antibiotic therapy, her blood cultures again grew Klebsiella organisms. She experienced spiking fevers up to 104.5°. An emergency CT scan of her body was performed with the hope of locating an abscess which could be drained in an attempt to improve her clinical condition. No abscess or other site of infection was found. She was then treated with XMMEN-OE5 monoclonal antibody 2 mg/kg (total dose 157 mg) i.v. over 2% hours. Twelve hours after infusion, her temperature was below 100°, and her clinical condition had improved markedly. Blood cultures were repeated and continued to grow gram negative organisms. Therefore, despite continued gram negative sepsis, her clinical condition improved markedly following the administration of monoclonal antibody. Her antibiotic regimen was then changed to a different combination of drugs, and her blood cultures subsequently became negative. She remained in improved condition 4 days after antibody therapy.

EXAMPLE II—HYBRIDOMA XMMEN-J5D

A. Production of XMMEN-J5D Hybridomas

The previous hybridoma protocol, except for the substitution of parental myeloma cell line SP2/0-Ag14 for P63Ag8.653, was employed to produce a second clone, designated XMMEN-J5D, which was found to stably secret a monoclonal antibody determined to be of immunoglobulin subclass IgG2a by the previously disclosed techniques. Hybridoma XMMEN-J5D was deposited with the A.T.C.C. on Apr. 24, 1986, and given A.T.C.C. Accession No. HB9083.

B. XMMEN-J5D MoAb Binding Activity as Determined by EIA

1. Detection of MoAb Binding to Whole Bacteria: Live bacteria were adjusted to $1.5 \times 10^8$/ml in normal saline. Flat bottom polyvinyl plates were coated with 50 ul/well of this suspension, then centrifuged for 30 minutes at 2000× g. Pelleted cells were fixed by the addition of 150 ul/well of 0.25% gluteraldehyde/PBS for 15 minutes at room temperature. Supernatants were discarded and the plates were then washed with PBS, then blocked overnight by adding 100 ul/well of 0.1% gelatin/PBS.

The plates were again washed and 100 ul/well of affinity purified XMMEN-J5D MoAb (1 ug/ml) was allowed to react with the coated antigen for one hour at RT. Following a PBS wash, goat anti-mouse IgG peroxidase conjugate (100 ul/well) was allowed to react for one hour at RT. After a final wash, ABTS substrate was added (100 ul/well), allowed to react for 45 minutes at RT, and absorbance at 405 nm recorded using a Titertek ELISA reader (Flow Labs, McLean, Va.). The results are summarized in Table 9.

TABLE 9

Enzyme Linked Immunosorbent Assay (EIA)
XMMEN-J5D MoAb Binding To Bacteria

| Bacteria | Absorbance @ 405 nm |
|---|---|
| Serratia marcescens | 0.10 |
| Enterobacter cloaceae | 0.07 |
| Acinetobacter calcoaceticus | 0.06 |
| Listeria monocytogenes | 1.15* |
| Salmonella minnesota R595 | 0.91* |
| Salmonella dublin | 0.09 |
| Salmonella arizona | 0.18 |
| Shigella boydii Type 3 | 0.11 |
| Klebsiella pneumoniae | 0.05 |
| Proteus mirabilis | 0.05 |
| Haemophilus influenzae | 0.51* |
| Providencia stuartii | 0.49* |
| Bacteroides fragilis | 1.39* |
| Neiseria meningitidis | 1.37* |
| Streptococcus pneumoniae | 1.43* |
| Micrococcus Species | 0.04 |
| Enterococcus Group K | 0.99* |
| Staphyloccus epidermidis | 0.18 |
| Pseudomonas cepacia | 3.19* |
| Pseudomonas pickettii | 3.19* |
| Pseudomanas putida | 3.20* |
| Pseudomonas maltophilia | 2.74* |
| Pseudomonas aeruginosa PAC 1R | 1.17* |
| Pseudomonas aeruginosa PAC 557 | 1.25* |
| Pseudomonas aeruginosa PAC 605 | 3.12* |
| Pseudomonas aeruginosa International Type 3 | 0.26 |
| Pseudomonas aeruginosa International Type 4 | 0.69* |
| Pseudomonas aeruginosa International Type 9 | 0.82* |
| Pseudomonas aeruginosa International Type 11 | 0.67* |
| Pseudomonas aeruginosa International Type 12 | 0.53* |
| Pseudomonas aeruginosa International Type 13 | 0.88* |
| Pseudomonas aeruginosa International Type 14 | 0.42* |
| Pseudomonas aeruginosa International Type 15 | 0.95* |
| Pseudomonas aeruginosa Fisher Type 2 | 0.21 |
| Pseudomonas aeruginosa Fisher Type 4 | 0.14 |
| Pseudomonas aeruginosa Fisher Type 6 | 0.47* |
| Pseudomonas aeruginosa Clinical Isolate # 4194 | 0.56* |
| Escherichia coli O14:H31 | 1.10* |
| Escherichia coli O14:K7 | 0.12 |
| Escherichia coli O4:K12 | 0.27 |
| Escherichia coli O9:K57:H32 | 0.21 |
| Escherichia coli O113:K75 | 0.10 |
| Escherichia coli J5-RR Serum Resistant Strains | 3.25* |
| Escherichia coli O85:H9 | 0.05 |
| Acinetobacter calcoaceticus Clinical Isolate # 7711 | 0.09 |
| Pseudomonas aeruginosa Fisher Type 1 | 0.20 |
| Pseudomonas aeruginosa Fisher Type 3 | 0.19 |
| Pseudomonas aeruginosa Fisher Type 7 Drug Resistant Strain | 0.11 |
| Pseudomonas aeruginosa Clinical Isolate # 3632 | 0.81* |

*clearly positive above background

2. Detection of MoAb Binding Lipopolysaccharide (LPS): Preparations of purified antigens were diluted to 25 ug/ml in either 0.05% triethylamine/H₂O or 0.05M MgCl₂/ PBS to see if solubility affected results. 100 ul/well of these antigens were coated onto 96-well, flat bottom polystyrene EIA plates. Following an overnight incubation at RT, the plates were blocked with 0.10% gelatin in 0.01M PBS for 2 hours at 37° C., then washed with 0.01M PBS.

Affinity purified XMMEN-J5D MoAb was diluted to 10 ug/ml in 0.10% gelatin/PBS and allowed to react with the coated antigens for one (1) hour at room temperature (RT). The plates were washed and 100 ul/well of goat anti-mouse IgG-peroxidase conjugate was incubated with the antigens at RT for one hour. After another washing step, positive reactions were detected by the addition of 100 ul/well of substrate: 2,2'azino-di-(3-athyl-benzthiazolinsulfonat(6)) (ABTS). Color development was allowed to proceed for 45 minutes, and optical density (O.D.) at 405 nm recorded. The results are summarized in Table 10.

TABLE 10

XMMEN-J5D Binding Activity To Lipopolysaccharide (LPS)

| | Absorbance @ 405 nm | |
|---|---|---|
| Antigen | LPS plus 0.05M MgCl₂/PBS | LPS plus 0.5% Triethylamine |
| Escherichia coli J5 (from List Biological) | 0.87 | 0.22 |
| Salmonella minnesota R60 (Ra) (from List Biological) | 1.35 | 1.70 |
| Salmonella minnesota R345 (Rb) (from List Biological) | 0.48 | 0.19 |
| Salmonella minnesota R5 (Rc) (from List Biological) | 0.16 | 0.05 |
| Salmonella minnesota R7 (Rd) (from List Biological) | 0.05 | 0.05 |
| Salmonella minnesota R595 (Re) (from List Biological) | 0.09 | 0.03 |
| Salmonella minnesota wild type (from List Biological) | 0.08 | 0.42 |
| Escherichia coli (from List Biological) | 0.02 | 0.22 |
| Escherichia coli (from List Biological) | 0.06 | 0.12 |
| Escherichia coli (from List Biological) | 0.06 | 1.65 |
| Escherichia coli (from List Biological) | 0.07 | 1.31 |
| Escherichia coli (from List Biological) | 0.04 | 0.11 |
| Escherichia coli (from List Biological) | 0.16 | 0.08 |
| Klebsiella Pneumoniae (from List Biological) | 0.05 | 0.03 |
| Serratia marcescens (from List Biological) | 0.00 | 0.02 |
| Acinetobacter calcoaceticus (LPS extracted according to the method of Darveau & Hancock, J. Bacte. (1983) 155:831 incorporated by reference) | 0.03 | 0.02 |
| Pseudomonas aeruginosa PAC 605 (LPS extracted according to the method of Darveau & Hancock) | 0.07 | 0.05 |
| Pseudomonas aeruginosa Fisher 1 (from Parke-Davis & Co.) | 0.05 | 0.04 |
| Pseudomonas aeruginosa Fisher 2 (from Parke-Davis & Co.) | 0.00 | 0.03 |
| Pseudomonas aeruginosa | 0.06 | 0.03 |

TABLE 10-continued

XMMEN-J5D Binding Activity To Lipopolysaccharide (LPS)

| | Absorbance @ 405 nm | |
|---|---|---|
| Antigen | LPS plus 0.05M MgCl$_2$/PBS | LPS plus 0.5% Triethylamine |
| Fisher 3 (from Parke-Davis & Co.) | | |
| Pseudomonas aeruginosa Fisher 4 (from Parke-Davis & Co.) | 0.00 | 0.03 |
| Pseudomonas aeruginosa Fisher 5 (from Parke-Davis & Co.) | 0.00 | 0.03 |
| Pseudomonas aeruginosa Fisher 6 (from Parke-Davis & Co.) | 0.00 | 0.03 |
| Pseudomonas aeruginosa Fisher 7 (from Parke-Davis & Co.) | 0.02 | 0.01 |

C. XMMEN-J5D Immunodot Serology

Antigens were applied to 0.20 μm cellulose nitrate membrane (Sartorius) as 1 μl "dots" and allowed to air dry for five minutes (concentration used was 100 μg/ml purified LPS in PBS). The antigen spotted membranes were then blocked with a 1% solution (wt/vol PBS) of gelatin (Difco, Detroit, Mich.), for 30 minutes at RT. Following a rapid (1 minute each, 2×) was, XMMEN-JD5 (2–5 μg/ml in PBS) was incubated with the membranes for 30 minutes at RT. The membranes were washed rapidly 3× with PBS, then incubated with goat anti-mouse IgG-peroxidase conjugate (Cappel, Malvern, Pa.) for 30 minutes at RT. After washing the membranes 3–4× with PBS, substrate (4-chloro-1-naphthol, Sigma Chemical Co., St. Louis, Mo.) was incubated with the membranes at RT. Positive reactions usually appeared as purple dots within 2–5 minutes, and were visually graded as 4+ (very strong) to 1+ (weak). The results are summarized in Table 11.

TABLE 11

XMMEN-J5D Immunodot Serology with Purified Lipopolysaccharide (LPS)

| Antigen | Reaction* |
|---|---|
| Salmonella minnesota R60 (Ra) | 3+ |
| Salmonella minnesota R345 (Rb) | 3+ |
| Escherichia coli J5 (Rc) | 1+ |
| Salmonella minnesota R7 (Rd) | — |
| Salmonella minnesota R595 (Rc) | — |
| Pseudomonas aeruginosa PAC 605 | — |
| Pseudomonas aeruginosa Fisher type 1 | — |
| Klebsiella pneumoniae | — |
| Acinetobacter calcoaceticus | — |

Pseudomonas aeruginosa PAC 605 LPS and Acinetobacter calcoaceticus LPS were purified according to Darveau al., J. Bacte. (1983) 155:831. All other LPS preparations were purchased from List Biologicals, Campbell, Calif.

E. In Vivo Efficacy of XMMEN-J5D MoAbs

1. Challenge Experiments: CD-1 female mice were injected i.p. with 150 ug of monoclonal antibody 24 hours before i.p. challenge with live bacteria. The results are summarized in Table 12.

TABLE 12

Summary of Challenge Experiments

| | Survivors (48 Hrs) | | |
|---|---|---|---|
| Challenge Organism | XMMEN-J5D MoAb | XMMPS-605 MoAb | Control |
| P. aeruginosa Fisher 1 | 2/5 | 1/5 | 1/5 |
| P. aeruginosa Fisher 2* | 3/5 | 4/5 | 1/5 |
| P. aeruginosa Fisher 3 | 0/5 | 0/5 | 0/5 |
| P. aeruginosa Fisher 4 | 5/5 | 4/5 | 1/5 |
| E. coli 04K12 | 4/5 | 5/5 | 1/5 |
| E. coli 014K7 | 1/10 | 1/5 | 0/5 |
| E. coli 085:H9 | 3/5 | — | 0/5 |
| E. coli 085:H9 | — | 3/5 | 2/5 |

*(3632 strain)

EXAMPLE III—HYBRIDOMA XMMPS-605

A. Production of XMMPS-605 Hybridomas

New Zealand Black mice (Jackson Laboratories, Bar Harbor, Me.) were immunized with 1×10$^8$ formalin-killed cells of Pseudomonas aeruginosa strain PAC 605 in Complete Freund's Adjuvant (Difco Laboratories, Detroit, Mich.). The LPS of PAC 605, a bacteriophage-resistant mutant of strain PAC 1R, lacks outer O-specific side chains and consists only of the core LPS (lipid A and core oligosaccharide), as shown by sodium dodecyl-sulfate-polyacrylamide gel electrophoresis (SDS-PAGE) analysis (Meado et al., J. of General Microbiology (1984) 130:631–644). After primary immunization, the mice were boosted with an intraperitoneal injection of 1×10$^8$ formalin-killed P. aeruginosa cells lacking O-specific side chains at one month intervals.

Four days following the last antigen boost, spleen cells from an immunized mouse were aseptically removed. Following procedures as outlined elsewhere (St. Groth, J. Immuno. Meth. (1908) 35:1), 5×10$^7$ spleen cells were fused with an equal number of SP2/O-AG14, a nonsecreting mouse myeloma cell line of Balb/c origin, using polyethylene glycol 4000 (American Type Culture Collection, Rockville, Md.). Hybrid cells were placed into 96-well culture plates (Costar, Cambridge, Mass., #3596) on medium which had been pre-incubated with a feeder layer of normal New Zealand Black thymocytes (1×10$^5$ cells per well, one day before fusion). Cells were cultured at 37° C., in a 10% CO$_2$ atmosphere, in the following medium for the first two weeks: Dulbecco's Modified Eagle's Medium, with glutamine, and glucose at 4.5 g/l (Gibco, Santa Clara, Calif., #320-1965), Fetal Bovine Serum (10%) (Microbiological Associates, Walkerville, Md.), sodium pyruvate (1 mM) (Gibco, Santa Clara, Calif., #320-1360), penicillin (50μ/ml) —Streptomycin (50μ/ml) (Gibco, Santa Clara, Calif., #600-5070), and hypoxanthine-aminopterin-thymidine (HAT) which was prepared by using 1.0% v/v (100×) hypoxanthine-thymidine supplement (Microbiological Associates, Walkersville, Md., #17-782A) combined with 0.04 mM aminopterin (Sigma Chemical Co., St. Louis, Mo.). Medium for regular maintenance (past two weeks fusion date) Was identical to the above, except that no aminopterin was included in the medium (HT medium).

Between two to four weeks post-fusion, cultures of hybrid cells were tested for antibody binding to P. aeruginosa purified LPS by EIA (as detailed in Example II) and immunodot assay (as detailed in Example VII). Cultures that were positive on repeated testing were then cloned by limiting dilution techniques. Briefly, the cells were cultured at dilutions varying from 10–1 cells per well in 96-well tissue culture plates (Costar, Cambridge, Mass., #3596). Wells that contained only one colony were identified by microscopic examination, then tested for anti-PAC 605 activity by EIA. Positive clones were expanded onto 24-well tissue cultures plates (Costar, Cambridge, Mass., #3524), recloned and retested by the same methods. A single clone, designated XMMPS-605, was found to stably secrete monoclonal antibody; the monoclonal antibody was determined to be of immunoglobulin class IgG2B by radial immunodiffusion and radioimmunoassay, using standard methods.

New Zealand Black mice (Jackson Laboratories, Bar Harbor, Me.) were used to culture the hybridomas interperitoneally. Approximately $3 \times 10^6$ hybridoma cells were injected intraperitoneally (i.p.) into mice that had been pretreated as follows: 1) injected i.p. one week earlier with 0.5 ml of pristane (Aldrich Chemical Co., Milwaukee, Wis.), and 2) injected i.p. one day earlier with 2 mg of cyclophosphamide (Adria Laboratories, Columbus, Ohio). The resultant ascites fluid, collected 11–15 days after injection of the hybridomas, contained on average 5 mg/ml of the anti-PAC 605 antibody, XMMPS-605, as determined by radial-immunodiffusion (Meloy, Radial Immunodiffusion, Springfield, Va., Plate #J-307), performed according to the method given in Meloy instruction sheet entitled "Quantitative Immunodiffusion Plates for Mouse Immunoglobulins," which is incorporated by reference.

The antibody in ascites fluid was purified by using a protein-A Sepharose C1-4B column (Pharmacia, Inc., Piscataway, N.J.) by methods well-known to those skilled in the art, as described elsewhere (Ey, *Immunochemistry* (1978) 15:429–436). Determination of immunoglobulin subclass (IgG2B) was accomplished by immunodot assay, using subclass specific antibody conjugated to peroxidase (Southern Biotechnology Associates, Inc., Birmingham, Ala.).

Hybridoma XMMPS-605 was deposited with the A.T.C.C. on Sep. 26, 1985, and given A.T.C.C. Accession No. HB 8909.

B. Enzyme-Linked Immunoassay (EIA) Using Whole Bacteria

Thirty gram negative bacteria strains were tested to determine the extent of cross-reactivity of XMMPS-605 monoclonal antibody. The sources of these strains were as follows: 1) *Salmonella minnesota* R595, chemotype Re, strain KNV, was acquired from Dr. Otto Westphal (Max Planck Institute fur Immunobiologie, Freiburg, Federal Republic of West Germany); 2) the international types of *Pseudomonas aeruginosa*, *E. coli* serotypes 055:55 and 026:B6 were purchased from the American Type Culture Collection (A.T.C.C.); 3) *P. aeruginosa* PAC 1R, PAC 557, PAC 605, from Pauline Meadow, (University College at London); 4) *P. aeruginosa* Fisher types 1–7 were donated from Dr. Matthew Pollack (Uniformed Services university, Bethesda, Md.); 5) *E. coli* 014:K7 was obtained from Dr. Erwin Neter and Dr. H. Y. Whang (Children's Hospital of Buffalo, N.Y.); 6) *E. coli* 085:H9 was obtained from the Center for Disease Control (Atlanta, Ga.); 7) the *Escherichia coli* J5 rough mutant was obtained from Dr. Abraham Braude (University of California, San Diego); 8) the remaining strains were clinical isolated #7711, #3632, #4194 from the UCLA Medical Center.

These bacteria were first cultured on trypticase-soy agar (TSA) plates. Bacterial cells were harvested and their concentration adjusted to $1.5 \times 10^8$ cells/ml in normal saline. Concentrations were determined by the measured absorbance (optical density) of the bacterial suspensions at 570 nanometers (nm). Fifty aliquots of these suspensions were coated onto wells of flat-bottom polyvinyl plates (Falcon LabWare, Oxnard, Calif., #3912), then centrifuged for 30 minutes at 2000× G. Pelleted cells were fixed by the addition of 150 µl/well of 0.25% gluteraldehyde/phosphate buffered saline 0.01M, pH 7.4 (hereinafter PBS) for 15 minutes at room temperature. Supernatants were discarded and the plates washed with PBS, and then blocked overnight at room temperature with 0.1% gelatin/TBS.

The remainder of the assay was identical to that described for EIA using LEPS (Example III). The plates were washed and 100 µl/well of affinity-purified XMMPS-605 monoclonal antibody (1 µg/ml) was allowed to react with the coated antigens for one hour at room temperature. Following a PBS wash, 100 µl/well of goat anti-mouse IgG-peroxidase conjugate was added and allowed to react for one hour at room temperature. After a final wash, 2-2'azino-di(3-athyl-benzthiazolin-sulfonate) (6) (ABTS) (Boehringer Mannheim Biochemicals, Indianapolis, Ind.), substrate was added (100 µl/well); color development proceeded for 15 minutes, at which point the absorbance at 405 nm was recorded as previously described.

The results of these assays are presented in Table 13. All strains of *Pseudomonas aeruginosa* and *P. maltophilia* exhibited significant absorbance at 405 nm (range 0.37 to 1.60 O.D.). Of the other strains of gram negative bacteria tested, none showed significant reactivity. The antigenic determinant of lipopolysaccharide with which the monoclonal antibody is reactive is therefore shown to be common to all strains of *P. aeruginosa* and to *P. maltophilia*, but is not present on other gram negative and gram positive bacteria.

TABLE 13

Enzyme-Linked Immunosorbent Assay (EIA) Of XMMPS-605 Binding To Whole Bacteria

| Bacteria | Absorbance At 405 nm |
| --- | --- |
| *Pseudomonas aeruginosa* PAC 1R | 0.75 O.D. |
| *Pseudomonas aeruginosa* PAC 557 | 1.60 O.D. |
| *Pseudomonas aeruginosa* PAC 605 | 1.60 O.D. |
| *Pseudomonas aeruginosa* Fisher Type 1 | 0.73 O.D. |
| *Pseudomonas aeruginosa* Fisher Type 2 | 0.76 O.D. |
| *Pseudomonas aeruginosa* Fisher Type 3 | 0.75 O.D. |
| *Pseudomonas aeruginosa* Fisher Type 4 | 1.52 O.D. |
| *Pseudomonas aeruginosa* Fisher Type 5 | 1.53 O.D. |
| *Pseudomonas aeruginosa* Fisher Type 6 | 0.41 O.D. |
| *Pseudomonas aeruginosa* Fisher Type 7 | 0.37 O.D. |
| *Pseudomonas aeruginosa* Intern'l Type 3 | 1.57 O.D. |
| *Pseudomonas aeruginosa* Intern'l Type 4 | 1.55 O.D. |
| *Pseudomonas aeruginosa* Intern'l Type 9 | 1.53 O.D. |
| *Pseudomonas aeruginosa* Intern'l Type 11 | 1.47 O.D. |
| *Pseudomonas aeruginosa* Intern'l Type 12 | 1.54 O.D. |
| *Pseudomonas aeruginosa* Intern'l Type 13 | 1.60 O.D. |
| *Pseudomonas aeruginosa* Intern'l Type 14 | 1.58 O.D. |
| *Pseudomonas aeruginosa* Intern'l Type 15 | 1.57 O.D. |
| *Pseudomonas cepacia* | 0.03 O.D. |
| *Pseudomonas pickettii* | 0.03 O.D. |
| *Pseudomonas putida* | 0.03 O.D. |
| *Pseudomonas maltophilia* | 1.34 O.D. |
| *Salmonella minnesota* R595 | 0.02 O.D. |
| *Escherichia coli* J5 | 0.02 O.D. |
| *Escherichia coli* 014:K7 | 0.01 O.D. |
| *Escherichia coli* 014:H31 | 0.02 O.D. |
| *Escherichia coli* 085:H9 | 0.00 O.D. |
| *Enterobacter cloaceae* | 0.02 O.D. |
| *Serratia marcescens* | 0.00 O.D. |
| *Klebsiella pneumoniae* | 0.01 O.D. |

C. Enzyme Linked Immunosorbent Assay (EIA) Using Purified Lipopolysaccharide (LPS)

A total of 24 different purified lipopolysaccharide extracts from the bacteria listed on Table 2 were used to determine the extent of cross-reactivity of the anti-PAC 605 monoclonal antibody, MS-605. The LPS of *P. aeruginosa* PAC 605 and that of *Acinetobacter calcoaceticus* (UCLA clinical isolate #7471) were extracted from the bacterial outer membranes according to published methods (Darveau, et al., *Jour. of Bacteriology* (1983) 155:831 which is incorporated by reference). Purified LPS from *P. aeruginosa* Fisher types 1–7 were obtained from Parke-Davis & Co. (Detroit, Mich.), and the remaining purified antigens were purchased from List Biologicals (Campbell, Calif.).

Preparations of these purified antigens were diluted to 25 μg/ml in water containing 0.5% triethylamine. One hundred μl/well of these antigens were coated onto 96-well EIA plates (Costar, Cambridge, Mass., #3590). Following overnight incubation at room temperature, the plates were blocked with 0.1% reagent grade gelatin (Difco, Inc., Detroit, Mich.) in PBS for two hours at 37° C. This step was essential to prevent nonspecific binding of the antibody to the polystyrene wells. The plates were then washed once with PBS.

Monoclonal antibody XMMPS-605 which had been affinity purified as indicated in Example I was diluted to 5 μg/ml in 0.1% gelatin/PBS and allowed to react with the coated antigen for one hour at room temperature. After three washings with PBS, 100 μl of the second antibody (goat anti-mouse IgG-peroxidase conjugate (Cappel, Malvern, Pa., #0600-3161)) was added to the reaction wells, and left to react at room temperature for one hour. The plates were again washed three times with PBS. Positive reactions were detected by adding ABTS (Boehringer Mannheim Biochemicals, Indianapolis, Ind.). This substrate was prepared by first making a stock solution of 20 mg/ml ABTS in 0.1M citrate buffer (pH 4.5). The solution was then diluted 1:50 in citrate buffer and to it was added a 1:1000 dilution of 30% hydrogen peroxide. Color development was allowed to proceed for 15 minutes, and the absorbance was read at 405 nm in a Titertek Elisa Reader (Flow Labs, McLean, Va.). The results of these assays are presented in Table 2, showing the XMMPS-605 antibodies bind only to LPS from *P. aeruginosa* and *P. maltophilia* after testing against LPS from a wide range of gram negative bacteria. The LPS of all seven of the Fisher strains of *Pseudomonas aeruginosa* and PAC 605 showed absorbance (range 0.78–1.06 O.D.). None of the LPS from the remaining gram negative bacteria tested showed significant absorbance.

Results of these assays are presented in Table 14. As can be seen therein, XMMPS-605 binds to all *P. aeruginosa* representing all Fisher groupings, as indicated by the relatively high levels of absorbance. None of the EPS from other species tested, including preparations of purified core region LPS, exhibited significant absorption.

TABLE 14

XMMPS-605 Binding Activity To Lipopolysaccharide (LPS) As Determined By Enzyme-Linked Immunoabsorbent Assay (EIA)

| Antigen | Absorbance At 405 nm |
| --- | --- |
| *Pseudomonas aeruginosa* PAC 605* | 0.78 O.D. |
| *Pseudomonas aeruginosa* Fisher 1 | 1.01 O.D. |
| *Pseudomonas aeruginosa* Fisher 2 | 1.05 O.D. |
| *Pseudomonas aeruginosa* Fisher 3 | 1.06 O.D. |
| *Pseudomonas aeruginosa* Fisher 4 | 0.95 O.D. |
| *Pseudomonas aeruginosa* Fisher 5 | 0.86 O.D. |
| *Pseudomonas aeruginosa* Fisher 6 | 0.86 O.D. |
| *Pseudomonas aeruginosa* Fisher 7 | 0.95 O.D. |
| *Salmonella minnesota* Wild Type | 0.02 O.D. |
| *Salmonella minnesota* R60 (Ra)* | 0.02 O.D. |
| *Salmonella minnesota* R345 (Rb)* | 0.08 O.D. |
| *Salmonella minnesota* R5 (Rc)* | 0.01 O.D. |
| *Salmonella minnesota* R7 (Rd)* | 0.03 O.D. |
| *Salmonella minnesota* R595 (Re)* | 0.01 O.D. |
| *Escherichia coli* J5 (Rc)* | 0.05 O.D. |
| *Escherichia coli* K235 | 0.00 O.D. |
| *Escherichia coli* 011:B4 | 0.00 O.D. |
| *Escherichia coli* 055:B5 | 0.00 O.D. |
| *Escherichia coli* 026:B6 | 0.00 O.D. |
| *Escherichia coli* 0127:B8 | 0.00 O.D. |
| *Escherichia coli* K12 | 0.01 O.D. |
| *Klebsiella pneumoniae* | 0.04 O.D. |
| *Serratia marcescens* | 0.01 O.D. |
| *Acinetobacter calcoaceticus* | 0.00 O.D. |

*LPS used in assay was a preparation of the core region isolated from mutants which do not express O-side chains.

D. Immunodot Assay Binding to Purified Lipopolysaccharide (LPS)

Purified LPS (100 μg/ml, PBS) was applied to cellulose nitrate membrane (0.20 μm, Sartorius, Hayward, Calif., #11307) as 1 μl "dots" and allowed to air dry for several minutes. The membranes were then blocked in 1.0% reagent grade gelatin/PBS for 30 minutes at room temperature. The remainder of the rapid, room temperature assay was accomplished as follows: Immersion of the antigen treated membranes in culture supernatant (containing XMMPS-605 monoclonal antibody) for 30 minutes, followed by a PBS wash; immersion in goat anti-mouse IgG-peroxidase conjugate for 30 minutes, followed by a PBS wash; immersion in 4-chloro-1-naphthol (Sigma Chemical Co., St. Louis, Mo.), substrate for color development of purple, positive "dots." Positive reactions usually occur within 5 minutes. Preparation of substrate: 4-chloro-1-naphthol was prepared as a 0.3% stock solution (w/v) in methanol, then diluted 1:5 in 0.01M PBS, to which was added a 1:1000 dilution of 30% hydrogen peroxide.

The dots were scored visually for positive reaction, using a scale of 4+ for strong color to 1+ for weak color. As indicated by the data presented in Table 15, LPS from all Fisher serotypes of *P. aeruginosa* gave a positive reaction (2+ or 3+) indicating binding by XMMPS-605, while no samples of LPS from other bacteria presented discernible color, indicating no binding by XMMPS-605.

TABLE 15

Immunodot Assay of XMMPS-605 Binding To Purified Lipopolysaccharides

| Antigen | Reaction |
| --- | --- |
| *Pseudomonas aeruginosa* PAC 605* | 2+ |
| *Pseudomonas aeruginosa* Fisher 1 | 3+ |
| *Pseudomonas aeruginosa* Fisher 2 | 3+ |
| *Pseudomonas aeruginosa* Fisher 3 | 3+ |
| *Pseudomonas aeruginosa* Fisher 4 | 3+ |
| *Pseudomonas aeruginosa* Fisher 5 | 3+ |
| *Pseudomonas aeruginosa* Fisher 6 | 3+ |
| *Pseudomonas aeruginosa* Fisher 7 | 3+ |
| *Salmonella minnesota* R60 (Ra)* | — |
| *Salmonella minnesota* R345 (Rb)* | — |
| *Salmonella minnesota* R7 (Rd)* | — |

TABLE 15-continued

Immunodot Assay of XMMPS-605 Binding To
Purified Lipopolysaccharides

| Antigen | Reaction |
|---|---|
| *Salmonella minnesota* R595 (Re)* | — |
| *Escherichia coli* J5 (Rc)* | — |
| *Escherichia coli* 055:B5 | — |
| *Klebsiella pneumoniae* | — |
| *Acinetobacter calcoaceticus* | — |

*LPS used in assay was a preparation of the core region isolated from mutants which do not express O-side chains.

E. Electrophoretic Transfer And Western Immunoblotting

The electrophoretic transfer of separated lysed whole cells and lipopolysaccharide components from SDS-PAGE gels to nitrocellulose sheet (Sartorius membranes) was adapted from the method of Towbin et al., *Proc. Nat. Acad. Sci. U.S.A.* (1979) 76:430–4354. The gels were placed in the Bio-Rad transblot electrophoretic transfer cell (Bio-Rad, Richmond, Calif.) containing 25 mM Tris, 19 mM glycine pH 8.3, 20% v/v methanol and 0.2% w/v/SDS. The nitrocellulose sheet was placed on gel toward the anode in order to transfer the image from the gel to the sheet. Electrotransfer using electrophoresis constant power supply (Pharmacia, Inc., Piscataway, N.J.) was carried out at 300 mA for 18 hours. After electrobotting, the nitrocellulose was washed in 0.01M phosphate buffered saline (PBS) at room temperature for 1 hour. The nitrocellulose sheet or strips were washed 3 times. Next, the sheet or strip was incubated for 1 hour with XMMPS-605 monoclonal antibody at a concentration of 20 μg XMMPS-605/ml in 0.01M PBS pH 7.2. The nitrocellulose sheet was washed twice for 10 minutes each and then incubated in a 1:400 goat anti-mouse IgG-peroxidase conjugate (Cappel Laboratories, Malvern, Pa.) (Fc fragment specific) for 1 hour. The nitrocellulose sheet was again washed 3 times as described above and the bound peroxidase conjugated second antibody was detected by soaking the nitrocellulose in the substrate-color-reagent 4-chloro-1-naphthol and hydrogen peroxide.

The standards used in the SDS-PAGE were: Cytochrome C (12.4 migration KD); Cytochrome C Dimer (24.8 migration KD); Cytochrone C Trimer (37.2 migration KD); Cytochrome C Tetramet (49.6 migration KD); and Cytochrome C HCX (74.4 migration KD). Molecular weights of bound components were determined relative to these standards.

A sodium dodecylsulfate-polyacrylamide gel electrophoresis (SDS-PAGE) analysis of whole cell extracts of *Pseudomonas aeruginosa* binding was done with XMMPS-605 by Western Immunoblot. The samples are as follows:

| Lane | *P. Aeruginosa* Serotype |
|---|---|
| 1 | Fisher 1 |
| 2 | Fisher 2 |
| 3 | Fisher 3 |
| 4 | Fisher 4 |
| 5 | Fisher 5 |
| 6 | Fisher 6 |
| 7 | PAC 605 |

For each sample, binding was shown to a low molecule weight component of the cell lysate which migrated to approximately 12 kilodaltons (kD).

A SDS-PAGE analysis of *P. aeruginosa* lipopolysaccharide binding with XMMPS-605 was done by Western Immunoblot. The samples are as follows:

| Lane | *P. Aeruginosa* Serotype |
|---|---|
| 1 | PAC 605 LPS |
| 2 | Fisher 1 LPS |
| 3 | Fisher 2 LPS |
| 4 | Fisher 4 LPS |

A binding pattern similar to that obtained with whole cell lysates was obtained, with binding to a low molecular weight component in the region of 12 kD. There is thus shown to be for all Fisher serotypes tested a common LPS component to which MS-605 selectively binds. Lane 7 and Lane 1 also show binding of MS-605 to a component of PAC 605 which migrates equivalently to a component of the Fisher strains, thus indicating that the antigenic determinant of the 12 kD component is in the core lipopolysaccharide rather than the O-specific side chains as PAC 605 does not express the O-specific side chains.

F. Polyacrylamide Gel Electrophoresis (SDS-PAGE) And Silver Staining

Sodium dodecyl sulfate gel electrophoresis was run using a modification of the method of Laemmli, *Nature* (1970) 227:680. The slab gels consisted of 10–20% linear acrylamide gradient with 1.6% bis in 3M Tris-HCl resolving buffer pH 8.8 and 4% acrylamide stacking gel in 0.5M Tris-HCl pH 6.8.

Washed live bacteria ($1\times10^{10}$ cells/ml) suspended in saline, and purified lipopolysaccharide samples in water (1 mg/ml) were mixed with equal parts of sample buffer containing 0.1M Tris-HCl, 2% w/v SDS, 10% v/v glycerol, 1% v/v 2-mercaptoethanol and 0.01% bromophenol blue. The mixtures were heated in a 100° C. water bath for 10 minutes and thirty microliters of sample were applied to slab gels. Electrophoresis was run at 35 mA per gel in Trisglycine buffer pH 8.8 until the tracking dye exited the gels.

The sensitive silver stain method of Tsai and Frasch, *Analyt. Biochem.* (1982) 119:115–119, was used to detect lipopolysaccharide in polyacrylamide gels. Electrophoretically resolved denatured whole cell components were stained according to the silver stain method of Morrissey, *Anal. Biochem.* (1981) 117:307.

G. Enhanced Opsonophagocytosis Of Bacteria In Presence Of Antibody

All seven Fisher serotypes of *Pseudomonas aeruginosa* were tested in vitro to determine their effect on certain aspects of the immune response with which a host would counteract a bacterial infection, such as opsonization and phagocytosis of invading cells. All bacteria were grown overnight on blood agar. After a visual check for purity, the isolates were transferred to Brain Heart Infusion Broth (BBL Microbiology Systems, Cockeysville, Md.) and grown for 4 hours at 37° C. with constant shaking. The bacteria were washed twice with Hanks Balanced Salt Solution (HBSS), and then brought to a concentration of $1\times10^8$ organisms/ml by comparing the turbidity to an appropriate McFarland standard.

Opsonophagocytosis was measured in a chemiluminescence assay using a Beckman LS-250 liquid scintillation spectrophotometer (Beckman Instruments, Inc., Fullerton, Calif.). Chemiluminescence is the light released by a white cell after it has engulfed a bacteria. The reaction was performed in the dark, using previously dark-adapted polypropylene scintillation vials. The vials contained 0.9 ml of HBSS, 0.1 ml of luminol ($2 \times 10^{-5}$M) and 0.075 ml of diluted human whole blood. The background was equilibrated for about 15 minutes, to reach approximately 15,000 CPM.

Heparinized blood was obtained from healthy donors. To 5 ml of blood, 1 ml of dextran (6%) was added. The erythrocytes were allowed to sediment for 60 minutes. The upper layer, containing the neutrophils, was centrifuged at 1000× G for 10 minutes. To lyse the remaining erythrocytes, the pellet was exposed to hypotonic saline (0.22%) for 30 seconds. Then, an equal volume of 1.54% saline was added to restore isotonicity. The neutrophils were suspended in HBSS and the final cell suspension adjusted to $2 \times 10^6$ cells/ml.

For each strain tested with XMMPS-605, a graph of counts per minutes (CPM) vs. time elapsed (minutes) was prepared. Numbers shown on Table 16 indicate maximum CPM values for each strain tested. The time at which maximum counts occurred varied according to strain, ranging from 30–80 minutes. These data indicate that for all serotypes except Fisher 1, phagocytosis is enhanced by the addition of XMMPS-605 above that obtained in the control sample containing only HBSS and in the samples containing only pooled human serum.

TABLE 16

Chemiluminescent Determination Of Opsonophagocytosis
XMMPS-605 Activity vs. *Pseudomonas aeruginosa*

| | Peak Counts × 10³ | | |
|---|---|---|---|
| Bacteria | HBSS (Control) | PHS | PHS + PCB5 |
| *P. aeruginosa* PAC 605 | 38 | 36 | 135 |
| *P. aeruginosa* Fisher type 1 | 38 | 36 | 36 |
| *P. aeruginosa* Fisher type 2 | 45 | 85 | 170 |
| *P. aeruginosa* Fisher type 3 | 22 | 60 | 98 |
| *P. aeruginosa* Fisher type 4 | 22 | 30 | 120 |
| *P. aeruginosa* Fisher type 5 | 38 | 82 | 120 |
| *P. aeruginosa* Fisher type 6 | 35 | 45 | 110 |
| *P. aeruginosa* Fisher type 7 | 40 | 50 | 135 |

HBSS = Hank's Balanced Salt Solution
PHS = Pooled Human Serum
XMMPS-605 MoAb: Concentration = 2 µg/ml As a confirmatory method of determining levels of cell death due to opsonization and phagocytosis, direct measurements of bacterial mortality were made. A test tube containing appropriate medium was innoculated with $2 \times 10^6$ polymorphonuclear cells/ml and $1.5 \times 10^7$ bacteria/ml (ratio 1:10). The tubes were incubated at 37° C. in a water bath. At 0, 60, and 120 minutes, dilutions were made in sterilized water and the number of colony forming units (CFU) growing on Trypticase-Soy Agar (TSA) plates were determined by counting microscopically. The results confirmed the opsonic activity of XMMPS-605 as demonstrated in the chemiluminescent assays. These results are summarized in Table 17.

TABLE 17

Measurement of Opsonophagocytosis By Cell Mortality Determination
PCB5 MoAb Activity vs. *Pseudomonas aeruginosa*

| | Colony forming units/ml × 10³* | | |
|---|---|---|---|
| Bacteria | Bacteria Only | PHS | PCB5 + PHS |
| *P. aeruginosa* Fisher type 1 | 78,000 | 6,800 | 6,800 |
| *P. aeruginosa* Fisher type 2 | 74,000 | 6,100 | 480 |
| *P. aeruginosa* Fisher type 3 | 74,000 | 6,400 | 530 |
| *P. aeruginosa* Fisher type 4 | 76,000 | 6,900 | 49 |
| *P. aeruginosa* Fisher type 5 | 78,000 | 6,400 | 550 |
| *P. aeruginosa* Fisher type 6 | 76,000 | 6,300 | 46 |
| *P. aeruginosa* Fisher type 7 | 75,000 | 590 | 49 |

*Counts of bacteria performed on tubes which were incubated for 60 minutes in a 37° C. water bath.
PHS = Pooled Human Serum
XMMPS-605: Concentration = 2 µg/ml

H. Use Of XMMPS-605 Monoclonal Antibody For Prophylaxis

150 µg of affinity purified XMMPS-605 monoclonal antibody was injected i.p. into 4-week-old CD-1 female mice (Charles River Breeding Labs, Inc., Wilmington, Mass.). Live bacteria were prepared as follows: strains of *P. aeruginosa* were grown in Brain Heart Infusion broth (BBL Microbiology Systems, Cockeysville, Md.) overnight at 37° C. The bacterial cells were washed twice with sterile saline, then adjusted to approximately $1 \times 10^9$ cells/ml saline, by comparing the optical density of the cell suspension to a standard curve relating absorbance to viable cell numbers. Approximately 18 hours after XMMPS-605 monoclonal antibody was injected, an approximate $LD_{100}$ dose of *Pseudomonas aeruginosa* cells was injected i.p. into experimental mice and control mice (which received the same protocol, but no XMMPS-605 monoclonal antibody). A previous dose-response study determined the $LD_{100}$, which was defined as the lowest dose that would kill 100% of the mice. Survivors were recorded at 48 hours. The results for individuals receiving Fisher 3 and 4 inoculation at a dosage of about $1 \times 10^8$ cells/individual indicate that pretreatment with XMMPS-605 conferred enhanced ability to survive the bacterial infection. These results are summarized in Table 18.

TABLE 18

Animal Studies: Prophylactic Treatment Of
*Pseudomonas Aeruginosa* Infection With XMMPS-605

| | Survivors | |
|---|---|---|
| Organism | XMMPS-605 Pretreatment | No Pretreatment |
| *P. aeruginosa* Fisher 1 (Dose = 1 × 10⁸ bacteria/individual) | 2/19 | 1/19 |
| *P. aeruginosa* Fisher 2 (Dose = 2.5 × 10⁸ bacteria/individual) | 4/29 | 3/29 |
| *P. aeruginosa* Fisher 3 (Dose = 1 × 10⁸ bacteria/individual) | 8/27(30%) | 4/27(15%) |
| *P. aeruginosa* Fisher 4 (Dose = 1 × 10⁸ bacteria/individual) | 13/27(48%) | 2/27(11%) |

EXAMPLE IV—HYBRIDOMA XMMPS-OP1

A. Production of XMMPS-OP1 Hybridomas

Balb/c mice (Charles Rivers, Wilmington, Mass.) were immunized with $1 \times 10^8$ boiled cells of *P. aeruginosa* Fisher Type 1. After primary immunization, the mice were boosted with an intraperitoneal injection of $1\times10^8$ boiled cells at one month intervals, for two months.

Four days following the last antigen boost, spleen cells from an immunized mouse were aseptically removed. Following procedures as outlined elsewhere (St. Groth, *J. Immuno. Meth.* (1980) 35:1), $5\times10^7$ spleen cells were fused with an equal number of SP2/0-Ag14, as previously described, using polyethylene glycol 4000 (Merck and Co., Inc., Rahway, N.J.). Hybrid cells were placed into 96-well culture plates (Costar, Cambridge, Mass. #3596) on medium which had been pre-incubated with a feeder layer of normal Balb/c thymocytes ($1\times10^5$ cells per well, one day before fusion). Cells were cultured at 37° C., in a 10% $CO_2$ atmosphere, in the following medium for the first two weeks. Dulbecco's Modified Eagle's Medium, with glutamine, and glucose at 4.5 g/l (Gibco, Santa Clara, Calif., #320–1965), Fetal Bovine Serum (10%) (Microbiological Associates, Walkerville, Md.), sodium pyruvate (1 mM) (Gibco, Santa Clara, Calif., #320-1360), penicillin (50μ/ml)—Streptomycin (50μ/ml) (Gibco, Santa Clara, Calif., #600-5070), and hypoxanthine-aminopterin-thymidine (HAT) which was prepared by using hypoxanthine (10 mM) thymidine (1.6 mM) combined with 0.04 mM aminopterin (Sigma Chemical Co., St. Louis, Mo.). Medium for regular maintenance (past two-weeks fusion date) was identical to the above, except that no aminopterin was included in the medium (HT medium).

Between two to four weeks post-fusion, cultures of hybrid cells were tested for antibody binding to purified LPS by EIA. Cultures that were positive on repeated testing were then cloned by limiting dilution techniques. Briefly, the cells were cultured at a concentration of between 10–1 cells per well in 96-well tissue culture plates (Costar, Cambridge, Mass., #3596). Wells that contained only one colony were identified by microscopic examination, then tested for anti-Fisher Type 1 activity by EIA. Positive clones were expanded onto 24-well tissue cultures plates (Costar, Cambridge, Mass. #3524), recloned and retested by the same methods. A clone, designated XMMPS-OP1, was found to stably secrete monoclonal antibody; the monoclonal antibody was determined to be of immunoglobulin class IgG1 by radial immunodiffusion and EIA using standard methods.

Balb/c mice (Charles River) were used to culture the hybridomas intraperitoneally. Approximately $3\times10^6$ hybridoma cells were injected intraperitoneally (i.p.) into mice that had been pretreated as follows: injected i.p. one week earlier with 0.5 ml of pristane (Aldrich Chemical Co., Milwaukee, Wis.). The resultant ascites fluid, collected 11–15 days after injection of the hybridomas, contained on average 5–20 mg/ml of the antibody, as determined by radial-immunodiffusion (Meloy, Radial Immunodiffusion, Springfield, Va., Plate #J-304).

The antibody in ascites fluid was purified by using a Protein A Sepharose C1-4B column (Pharmacia, Inc., Piscataway, N.J.) by methods well-known to those skilled in the art, as described elsewhere (Ey, *Immunochemistry* (1978) 15:429–436). Determination of immunoglobulin subclass (IgG1) was accomplished by EIA using rabbit anti-mouse subclass antibody (Miles Labs, Naperville, Ill.) and anti-rabbit Ig conjugated to peroxidase (Cappel, Malvern, Pa.).

EXAMPLE V—HYBRIDOMA XMMPS-OP2

A. Production of XMMPS-OP2 Hybridomas

Balb/c mice (Charles Rivers, Wilmington, Mass.) were immunized with $1\times10^8$ boiled cells of *P. aeruginosa* Fisher Type 2. After primary immunization, the mice were boosted with an intraperitoneal injection of $1\times10^8$ boiled cells at one month intervals, for two months.

Four days following the last antigen boost, spleen cells from an immunized mouse were aseptically removed. Following procedures as outlined elsewhere (St. Groth, *J. Immuno. Meth.* (1980) 35:1), $5\times10^7$ spleen cells were fused with an equal number of P63Ag8.653 as previously described, using polyethylene glycol 4000 (Merck and Co., Inc., Rahway, N.J.). Hybrid cells were placed into 96-well culture plates (Costar, Cambridge, Mass. #3596) on medium which had been pre-incubated with a feeder layer of normal Balb/c thymocytes ($1\times10^5$ cells per well, one day before fusion). Cells were cultured at 37° C., in a 10% $CO_2$ atmosphere, in the following medium for the first two weeks. Dulbecco's Modified Eagle's Medium, with glutamine, and glucose at 4.5 g/l (Gibco, Santa Clara, Calif., #320-1965), Fetal Bovine Serum (10%) (Microbiological Associates, Walkerville, Md.), sodium pyruvate (1 mM) (Gibco, Santa Clara, Calif., #320-1360), penicillin (50μ/ml)—Streptomycin (50μu/ml) (Gibco, Santa Clara, Calif., #600-5070), and hypoxanthine-aminopterin-thymidine (HAT) which was prepared by using hypoxanthine (10 mM) thymidine (1.6 mM) combined with 0.04 mM aminopterin (Sigma Chemical Co., St. Louis, Mo.). Medium for regular maintenance (past two-weeks fusion date) was identical to the above, except that no aminopterin was included in the medium (HT medium).

Between two to four weeks post-fusion, cultures of hybrid cells were tested for antibody binding to purified LPS by EIA. Cultures that were positive on repeated testing were then cloned by limiting dilution techniques. Briefly, the cells were cultured at dilutions of 10–1 cells per tell in 96-well tissue culture plates (Costar, Cambridge, Mass., #3596). Wells that contained only one colony were identified by microscopic examination, then tested for anti-activity by EIA. Positive clones were expanded onto 24-well tissue cultures plates (Costar, Cambridge, Mass.#3524), recloned and retested by the same methods. A clone, designated XMMPS-OP2, was found to stably secrete monoclonal antibody; the monoclonal antibody was determined to be of immunoglobulin class IgM by radial immunodiffusion and EIA using standard methods.

Balb/c mice (Charles River) were used to culture the hybridomas intraperitoneally. Approximately $3\times10^6$ hybridoma cells were injected intraperitoneally (i.p.) into mice that had been pretreated as follows: injected i.p. one week earlier with 0.5 ml of pristane (Aldrich Chemical Co., Milwaukee, Wis.). The resultant ascites fluid, collected 11–15 days after injection of the hybridomas, contained on average 2 mg/ml of the antibody, as determined by radial-immunodiffusion (Meloy, Radial Immunodiffusion, Springfield, Va., Plate #J-304).

EXAMPLE VI—HYBRIDOMA XMMPS-OP3

A. Production of XMMPS-OP3 Hybridomas

Balb/c mice (Charles Rivers, Wilmington, Mass.) were immunized with $1\times10^8$ boiled cells of *P. aeruginosa* Fisher Type 3. After primary immunization, the mice were boosted with an intraperitoneal injection of $1\times10^8$ boiled cells at one month intervals, for two months.

Four days following the last antigen boost, spleen cells from an immunized mouse were aseptically removed. Following procedures as outlined elsewhere (St. Groth, *J. Immuno. Meth.* (1980) 35:1), $5\times10^7$ spleen cells were fused with an equal number of SP2/0-Ag14, as previously described, using polyethylene glycol 4000 (Merck and Co., Inc., Rahway, N.J.). Hybrid cells were placed into 96-well culture plates (Costar, Cambridge, Mass. #3596) on medium which had been pre-incubated with a feeder layer of normal Balb/c thymocytes ($1 \times 10^5$ cells per well, one day before fusion). Cells were cultured at 37° C., in a 10% $CO_2$ atmosphere, in the following medium for the first two weeks. Dulbecco's Modified Eagle's Medium, with glutamine, and glucose at 4.5 g/l (Gibco, Santa Clara, Calif., #320-1965), Fetal Bovine Serum (10%) (Microbiological Associates, Walkerville, Md.), sodium pyruvate (1 mM) (Gibco, Santa Clara, Calif., #320-1360), penicillin (50μ/ml) —Streptomycin (50μ/ml) (Gibco, Santa Clara, Calif., #600-5070), and hypoxanthine-aminopterin-thymidine (HAT) which was prepared by using hypoxanthine (10 mM) thymidine (1.6 mM) combined with 0.04 mM aminopterin (Sigma Chemical Co., St. Louis, Mo.). Medium for regular maintenance (past two-weeks fusion date) was identical to the above, except that no aminopterin was included in the medium (HT medium).

Between two to four weeks post-fusion, cultures of hybrid cells were tested for antibody binding to purified LPS by EIA. Cultures that were positive on repeated testing were then cloned by limiting dilution techniques. Briefly, the cells were cultured at dilutions of 10–1 cells per well in 96-well tissue culture plates (Costar, Cambridge, Mass., #3596). Wells that contained only one colony were identified by microscopic examination, then tested for anti-activity by EIA. Positive clones were expanded onto 24-well tissue cultures plates (Costar, Cambridge, Mass. #3524), recloned and retested by the same methods. A clone, designated XMMPS-OP3, was found to stably secrete monoclonal antibody; the monoclonal antibody was determined to be of immunoglobulin class IgM by radial immunodiffusion and EIA using standard methods.

Balb/c mice (Charles River) were used to culture the hybridomas intraperitoneally. Approximately $3 \times 10^6$ hybridoma cells were injected intraperitoneally (i.p.) into mice that had been pretreated as follows: injected i.p. one week earlier with 0.5 ml of pristane (Aldrich Chemical Co., Milwaukee, Wis.). The resultant ascites fluid, collected 11–15 days after injection of the hybridomas, contained on average 2 mg/ml of the antibody, as determined by radial-immunodiffusion (Meloy, Radial Immunodiffusion, Springfield, Va., Plate #J-304).

EXAMPLE VII—HYBRIDOMA XMMPS-OP4

A. Production of XMMPS-OP4 Hybridomas

Balb/c mice (Charles Rivers, Wilmington, Mass.) were immunized with $1 \times 10^8$ boiled cells of *P. aeruginosa* Fisher-Type 4. After primary immunization, the mice were boosted with an intraperitoneal injection of $1 \times 10^8$ boiled cells at one month intervals, for two months.

Four days following the last antigen boost, spleen cells from an immunized mouse were asceptically removed. Following procedures as outlined elsewhere (St. Groth, *J. Immuno. Meth.* (1980) 35:1), $5 \times 10^7$ spleen cells were fused with an equal number of SP2/0-Ag14, as previously described, using polyethylene glycol 4000 (Merck and Co., Inc., Rahway, N.J.). Hybrid cells were placed into 96-well culture plates (Costar, Cambridge, Mass. #3596) on medium which had been pre-incubated with a feeder layer of normal Balb/c thymocytes ($1 \times 10^5$ cells per well, one day before fusion). Cells were cultured at 37° C., in a 10% $CO_2$ atmosphere, in the following medium for the first two weeks. Dulbecco's Modified Eagle's Medium, with glutamine, and glucose at 4.5 g/l (Gibco, Santa Clara, Calif., #320-1965), Fetal Bovine Serum (10%) (Microbiological Associates, Walkerville, Md.), sodium pyruvate (1 mM) (Gibco, Santa Clara, Calif., #320-1360), penicillin (50μ/ml) —Streptomycin (50μ/ml) (Gibco, Santa Clara, Calif., #600-5070), and hypoxanthine-aminopterin-thymidine (HAT) which was prepared by using hypoxanthine (10 mM) thymidine (1.6 mM) combined with 0.04 mM aminopterin (Sigma Chemical Co., St. Louis, Mo.). Medium for regular maintenance (past two-weeks fusion date) was identical to the above, except that no aminopterin was included in the medium (HT medium).

Between two to four weeks post-fusion, cultures of hybrid cells were tested for antibody binding to purified LPS by EIA and immunodot assay. Cultures that were positive on repeated testing were then cloned by limiting dilution techniques. Briefly, the cells were cultured at dilutions of 10–1 cells per well in 96-well tissue culture plates (Costar, Cambridge, Mass., #3596). Wells that contained only one colony were identified by microscopic examination, then tested for anti-activity by EIA. Positive clones were expanded onto 24-well tissue cultures plates (Costar, Cambridge, Mass. #3524), recloned and retested by the same methods. A clone, designated XMMPS-OP4, was found to stably secrete monoclonal antibody; the monoclonal antibody was determined to be of immunoglobulin class IgM by radial immunodiffusion and EIA using standard methods.

Balb/c mice (Charles River) were used to culture the hybridomas intraperitoneally. Approximately $3 \times 10^6$ hybridoma cells were injected intraperitoneally (i.p.) into mice that had been pretreated as follows: injected i.p. one week earlier with 0.5 ml of pristane (Aldrich Chemical Co., Milwaukee, Wis.). The resultant ascites fluid, collected 11–15 days after injection of the hybridomas, contained on average 2 mg/ml of the antibody, as determined by radial-immunodiffusion (Meloy, Radial Immunodiffusion, Springfield, Va., Plate #J-304).

EXAMPLE VIII—HYBRIDOMA XMMPS-OP7

A. Production of XMMPS-OP7 Hybridomas

Balb/c mice (Charles Rivers,. Wilmington, Mass.) were immunized with $1 \times 10^8$ boiled cells of *P. aeruginosa* Fisher Type 7. After primary immunization, the mice were boosted with an intraperitoneal injection of $1 \times 10^8$ boiled cells at one month intervals, for two months.

Four days following the last antigen boost, spleen cells from an immunized mouse were asceptically removed. Following procedures as outlined elsewhere (St. Groth, *J. Immuno. Meth.* (1980) 35:1), $5 \times 10^7$ spleen cells were fused with an equal number of SP2/0-Ag14, as previously described, using polyethylene glycol 4000 (Merck and Co., Inc., Rahway, N.J.). Hybrid cells were placed into 96-well culture plates (Costar, Cambridge, Mass. #3596) on medium which had been pre-incubated with a feeder layer of normal Balb/c thymocytes ($1 \times 10^5$ cells per well, one day before fusion). Cells were cultured at 37° C., in a 10% $CO_2$ atmosphere, in the following medium for the first two weeks. Dulbecco's Modified Eagle's Medium, with glutamine, and glucose at 4.5 g/l (Gibco, Santa Clara, Calif., #320-1965), Fetal Bovine Serum (10%) (Microbiological Associates, Walkerville, Md.), sodium pyruvate (1 mM) (Gibco, Santa Clara, Calif., #320-1360), penicillin (50μ/ml)

—Streptomycin (50μ/ml) (Gibco, Santa Clara, Calif., #600-5070), and hypoxanthine-aminopterin-thymidine (HAT) which was prepared by using hypoxanthine (10 mM) thymidine (1.6 mM) combined with 0.04 mM aminopterin (Sigma Chemical Co., St. Louis, Mo.). Medium for regular maintenance (past two-weeks fusion date) was identical to the above, except that no aminopterin was included in the medium (HT medium).

Between two to four weeks post-fusion, cultures of hybrid cells were tested for antibody binding to purified PPS by EIA and immunodot assay. Cultures that were positive on repeated testing were then cloned by limiting dilution techniques. Briefly, the cells were cultured at dilutions of 10–1 cells per well in 96-well tissue culture plates (Costar, Cambridge, Mass., #3596). wells that contained only one colony were identified by microscopic examination, then tested for anti-activity by EIA. Positive clones were expanded onto 24-well tissue cultures plates (Costar, Cambridge, Mass. #3524), recloned and retested by the same methods. A clone, designated XMMPS-OP7, was found to stably secrete monoclonal antibody; the monoclonal antibody was determined to be of immunoglobulin class IgG by radial immunodiffusion and EIA using standard methods.

Balb/c mice (Charles River) were used to culture the hybridomas intraperitoneally. Approximately $3 \times 10^6$ hybridoma cells were injected intraperitoneally (i.p.) into mice that had been pretreated as follows: injected i.p. one week earlier with 0.5 ml of pristane (Aldrich Chemical Co., Milwaukee, Wis.). The resultant ascites fluid, collected 11–15 days after injection of the hybridomas, contained on average 5–10 mg/ml of the antibody, as determined by radial-immunodiffusion (Meloy, Radial- Immunodiffusion, Springfield, Va., Plate #J-304).

EXAMPLE IX—IMMUNODOT SEROLOGY OF ANTI-P. AERUGINOSA LISPER TYPE MoAbs

Antigens were applied to 0.20 μm cellulose nitrate membrane (Sartorius) as 1 μm "dots" and allowed to air dry for five minutes. (Concentration used was 100 μg/ml purified LPS in PBS). The antigen spotted membranes were then blocked with a 1% solution (wt/vol PBS) of gelatin (Difco, Detroit, Mich.), for 30 minutes at RT. Following a rapid (1 minute each, 2×) wash, the appropriate anti-*Pseudomonas aeruginosa* MoAb was incubated with the membranes for 30 minutes at RT. (The MoAb was applied in this assay as a tissue culture supernatant at approximately 2–10 μg/ml). The membranes were washed rapidly 3× with PBS, then incubated with goat anti-mouse peroxidase conjugate (either anti-mouse IgM or IgG, as appropriate) (Cappel, Malvern, Pa.) for 30 minutes at RT. After washing the membranes 3–4× with PBS, substrate (4-chloro-1-naphthol, Sigma Chemical Co., St. Louis, Mo.) was incubated with the membranes at RT. Positive reactions usually appeared as purple dots within 2–5 minutes, and were usually graded as 4+ (very strong) to 1+ (weak). The results are summarized in Table 19.

TABLE 19

Immunodot Serology of Anti-Pseudomonas MoAbs With Purified Lipopolysaccharide (LPS)

| MoAbs | Antigens* | | | | | | |
|---|---|---|---|---|---|---|---|
| | Type 1 | Type 2 | Type 3 | Type 4 | Type 5 | Type 6 | Type 7 |
| XMMPS-OP1 | 3+ | — | — | — | — | — | — |
| XMMPS-OP2 | — | 3+ | — | — | — | — | — |
| XMMPS-OP3 | — | — | 3+ | — | — | — | 1+ |
| XMMPS-OP4 | — | — | — | 3+ | — | — | — |
| XMMPS-OP7 | — | — | 1+ | — | — | — | 3+ |

*Purified LPS from *Pseudomonas aeruginosa* Fisher types 1–7 obtained from Parke-Davis & Co., (Detroit, MI).
Reactions graded as 4+ (strong) to 1+ (weak).

EXAMPLE X—SUMMARY OF MoAb BINDING

The following table provides a summary of the binding characteristics of the MoAbs of the present invention. This table characterizes the MoAbs by their known antigens and not epitopes which are, for the most part, as yet uncharacterized.

TABLE 20

Summary of MoAb Binding

| MoAb | ANTIGENS | | |
|---|---|---|---|
| | Rough LPS | Smooth LPS | Whole cell |
| XMMEN-OE5 (IgM) | inner-core Rc, Rd, Re, lipid-A | NONE | strong reaction: rough *E. coli*, *P. aeruginosa* moderate reaction: some smooth *E. coli*, *P. aeruginosa* |
| XMMEN-LY1 (IgM) XMMEN-LY2 (IgM) | inner-core Rc, Rd, Re lipid-A | NONE | *S. minnesota* R595 |
| XMMEN-J5D (IgG2A) | outer core Ra, Rb, Rc | *E. coli* 011:B4 (western blot) | variety |
| XMMPS-605 (IgG2B) | *P. aeruginosa* PAC 605 core | all *P. aeruginosa* | all *P. aeruginosa* |
| XMMPS-OP1 (IgG1) | NONE | *P. aeruginosa* Fisher type 1 | *P. aeruginosa* Fisher type 1 |
| XMMPS-OP2 (IgM) | NONE | *P. aeruginosa* Fisher type 2 | *P. aeruginosa* Fisher type 2 |
| XMMPS-OP3 (IgM) | NONE | *P. aeruginosa* Fisher type 3 greater than type 7 | *P. aeruginosa* Fisher type 3 greater than type 7 |
| XMMPS-OP4 (IgM) | NONE | *P. aeruginosa* Fisher type 4 | *P. aeruginosa* Fisher type 4 |
| XMMPS-OP7 (IgG) | NONE | *P. aeruginosa* Fisher type 7 greater than type 3 | *P. aeruginosa* Fisher type 7 greater than type 3 |

EXAMPLE XI—IMAGING OF LOCALIZED BACTERIAL INFECTION

Monoclonal antibodies which react selectively with an antigenic determinant common to strains of infecting bacteria were utilized to determine the location and extent of a localized bacterial infection, especially those caused by gram negative bacteria, by methods well-known in the art, for example, Larson, et al., *Journal of Clinical Investigation* (1983) 72:2102, which is incorporated by reference. Monoclonal antibodies are preferably radiolabelled by radioiodination or by other radiolabelling techniques well-known in the art, such as chelation using a chelating agent such as diethylenetriaminepenta-acetic acid (DTPA); or are otherwise labelled, such as with agents having paramagnetic properties, with chemiluminescent substrates, or with components of an enzymatic reaction. The radiolabelled monoclonal antibodies are purified and formulated for pharmaceutical use. A solution of the labelled monoclonal antibodies in a carrier, for example in phosphate buffered saline, is injected intravenously into a host. The appropriate dose is in the range of about 100 µg to 50 mg. Time is permitted for the antibodies to migrate to regions of the body having concentrations of cells with antigenic determinants reactive therewith. Concentrations of radioisotopes in certain tissues are determined or may be mapped either by techniques of whole body imaging which are well-known in the art (See, for example, Rainsbury, et al., *Lancet* Oct. 22, 1983, 934 which is incorporated by reference), or by evaluating biopsied tissue or extracted body fluid using a scintillation counter. Where non-radioactive labels are used, other appropriate monitoring means are employed, such as a detector of nuclear magnetic resonance or a spectrophotometer. Areas of high radiation levels are indicative of the presence of localized bacterial infection.

EXAMPLE XII—THERAPEUTIC TREATMENT OF BACTERIAL INFECTION

Hosts determined to have a bacterial infection are treated with monoclonal antibodies reactive with an antigenic determinant common to all strains of the bacterium. The monoclonal antibodies are administered venously, intramuscularly, intraperitoneally, or the like, in a physiologically acceptable carrier solution, such as phosphate buffered saline. The dosage is determined by the body weight of the host, it preferably being in the range of about 0.1 mg/kg to about 40 mg/kg body weight, and usually about 1 mg/kg to about 10 mg/kg of host body weight. Alternatively, the dosage is established by evaluating the extent of the remaining infection, as by quantitatively standardized EIA radioimaging or other methods. Treatment is repeated at intervals as necessary, to effect enhancement of the hosts' ability to recover from the infection.

EXAMPLE XIII—DIAGNOSTIC EIA

Monoclonal antibodies of the present invention, or their functional equivalents, are utilized in an immunoassay using standard and well-known methods (for example, *Methods in Immunodiagnosis*, 2nd Edition, Rose and Bigazzi, eds., John Wiley and Sons., 1980). Such assay may be, for example, of direct format (labelled first antibody reactive with the antigen), an indirect format (a labelled second antibody reactive with the first antibody), a competitive format (for example, addition of labelled antigen), or a sandwich format (both labelled and unlabelled antibody), as well as other formats well-known in the art.

In one such embodiment, a tissue extract from a patient suspected of having a bacterial infection is applied to an insoluble matrix or solid substrate, such as cellulose strips, agarose or other particles so as to produce a bacteria-substrate complex. Alternatively, the substrate may have attached thereto an antibody so as to effect attachment of bacteria from a solution onto the substrate. The substrate is then washed, preferably with PBS, to remove unbound materials.

In a preferred embodiment, the solid substrate with bacteria attached is exposed to a solution having therein XMMPS-605, or other monoclonal antibody specific to *P. aeruginosa* and not reactive with other gram negative bacteria which might represent the causative agent of the bacterial infection. Such solutions include tissue extracts, serum and urine. The monoclonal antibody is allowed to react with the substrate complex and the complex then washed to remove any unbound monoclonal antibody. The substrate complex is then exposed to a solution having therein a labelled antibody reactive with the monoclonal antibody, such as goat anti-mouse IgG. This antibody is preferably labelled with a radioisotope, such as $^{131}$I, or more preferably with a component of an enzymatic reaction, such as peroxidase, but may also be labelled with a chemiluminescent substrate. The substrate is again washed to remove any unbound antibody. Monitoring means appropriate to the label, such as a scintillation counter or spectrophotometer, are used to determine the presence of label complexed to the substrate, indicative of the presence of *P. aeruginosa* or *P. maltophilia* in the tissue extract.

In addition to use for analyzing solutions of animal origin, similar methods are used to detect the presence of these bacteria on other objects or in other solutions in which *P. aeruginosa* or *P. maltophilia* contamination would be detrimental. Examples of such objects include medical devices for use in invasive procedures, respiratory ventilators, nebulizing humidifiers, oral thermometers, bedside water decanters and even jet fuel.

EXAMPLE XIV—PANEL EIA

Monoclonal antibodies of the present invention are supplied in a kit for performing an EIA panel for the characterization of the nature of a bacterial infection in a host. The individual MoAbs are used to perform an EIA as in Example XIII; however, the multiple EIA's employing a panel of MoAbs permits broad characterization of the bacteria causing the infection, including characterization of gram negative and gram positive bacteria.

EXAMPLE XV—QUANTIFICATION OF MICROBIAL ENDOTOXINS

The MoAbs of the present invention are employed in a method for the quantification of microbial endotoxins in body fluids, secretions and extracts or in drugs, diagnostic agents or liquid intermediates produced in the manufacture of diagnostic and therapeutic agents.

An IgM MoAb which possesses a binding specificity for a specific and unique determinant on endotoxin, such as XMMEN-OE5, is adsorbed to a solid surface. Removal of excess unadsorbed material is followed by blockage of potential additional nonspecific binding sites on the solid surface by an appropriate blocking reagent such as albumin. Unbound albumin is removed by simple washing procedures. The activated surface may be exposed to various concentrations of the test sample for varying periods of time ranging from one hour to 24 hours and at various incubation temperatures ranging from 4° to 37° C. Removal of unreacted or depleted test sample is accomplished by simple washing procedures with standard biochemical solutions such as buffered saline. Detection and quantification of endotoxin levels in the test solution is accomplished by the addition of a detection probe or binding partner, a second MoAb which belongs to the IgG subclass and possesses a binding specificity for a specific and unique determinant as endotoxin which is different from that bound by the IgM MoAb and which is not significantly affected in this system by the IgM absorbed to the solid surface.

Quantification is accomplished by relating the amount of the detection probe bound to the test sample to the amount of the detection probe bound to a defined quantity of an endotoxin reference standard. Assessment of the amount of the detection probe bound to the reference. standard the test sample is accomplished in a variety of ways such as: (a) radiolabeling of the probe and determination of radioactivity bound, (b) enzymatic labeling of the probe and measurement of enzymatic activity associated with specific amounts of the probe bound to the reference standard and test sample, (c) direct coupling to the probe of certain specific wavelengths emitting substances such as fluorochromes and quantification and comparison of these emissions by the standard reference and test samples. Quantification is also accomplished by labeling the detection probe with a substance such as biotin which allows the system to incorporate a standard second highly specific indicator such as avidin labeled with a radioisotope, enzyme, or fluorochrome.

In another embodiment of this system a second specific indicator consisting of radiolabeled, enzyme labeled, or fluorochrome labeled antibody specifically reactive with mouse Ig may be used to quantify the amount of endotoxin.

An advantage to initial adsorption of the IgM monoclonal antibody to the solid surface derives from the high binding avidity associated with antibodies belonging to the IgM class. This diminishes the level of endotoxin which might be lost from the primary binding liquid during the assay process.

The present invention provides pan-reactive MoAbs useful in the diagnosis, treatment and prevention of bacterial infection. The MoAbs of the invention have particular utility in blocking gram negative endotoxin, thus reducing its detrimental effects in hosts infected with gram negative bacteria.

Although the present invention has been described in some detail by way of illustration and example for purposes of clarity of understanding, it will be obvious that certain changes and modifications may be practiced within the scope of the appended claims.

What is claimed is:

1. A method for therapeutically treating a human having a gram negative bacterial infection, comprising administering to the human a therapeutically effective amount of an anti-lipid A region monoclonal antibody of the IgM isotype which competitively inhibits the binding of the monoclonal antibody produced by the hybridoma cell line ATCC Accession No. HB9081 to purified lipopolysaccharide from the J5 mutant of *E. coli* as measured by an enzyme immunoassay or other competitive inhibition immunoassay wherein the monoclonal antibody is administered in conjunction with antibiotic therapy.

2. A method for therapeutically treating a human having a gram negative bacterial infection, comprising administering to the human a therapeutically effective amount of an anti-lipid A region monoclonal antibody of the IgM isotype which competitively inhibits the binding of the monoclonal antibody produced by the hybridoma cell line ATCC Accession No. HB9081 to purified lipid A from the lipopolysaccharide of the J5 mutant of *E. coli* as measured by an enzyme immunoassay or other competitive inhibition immunoassay wherein the monoclonal antibody is administered in conjunction with antibiotic therapy.

* * * * *